(12) United States Patent
Satyanarayana Reddy et al.

(10) Patent No.: US 8,987,444 B2
(45) Date of Patent: Mar. 24, 2015

(54) PROCESS FOR THE PREPARATION OF AMIDE INTERMEDIATES AND THEIR USE THEREOF

(75) Inventors: Manne Satyanarayana Reddy, Hyderabad (IN); Srinivasan Thirumalai Rajan, Hyderabad (IN); Maramreddy Sahadeva Reddy, Hyderabad (IN)

(73) Assignee: MSN Laboratories Private Limited, Medak District, Telangana (IN)

( * ) Notice: Subject to any disclaimer, the term of this patent is extended or adjusted under 35 U.S.C. 154(b) by 211 days.

(21) Appl. No.: 13/522,591

(22) PCT Filed: Jan. 17, 2011

(86) PCT No.: PCT/IN2011/000034
§ 371 (c)(1),
(2), (4) Date: Jul. 17, 2012

(87) PCT Pub. No.: WO2011/086584
PCT Pub. Date: Jul. 21, 2011

(65) Prior Publication Data
US 2012/0323005 A1 Dec. 20, 2012

(30) Foreign Application Priority Data

Jan. 18, 2010 (IN) .............................. 124/CHE/2010
Mar. 1, 2010 (IN) .............................. 515/CHE/2010

(51) Int. Cl.
*C07D 239/02* (2006.01)
*C07D 405/06* (2006.01)

(52) U.S. Cl.
CPC ..................................... *C07D 405/06* (2013.01)
USPC ......................................................... 544/297

(58) Field of Classification Search
CPC ....................................................... C07D 239/02
USPC ......................................................... 544/297
See application file for complete search history.

(56) References Cited

U.S. PATENT DOCUMENTS

| 3,609,152 | A | * | 9/1971 | Hess et al. ...................... 540/600 |
| 4,337,341 | A | * | 6/1982 | Zimmerman ................. 546/112 |
| 4,739,073 | A | | 4/1988 | Kathawala |
| 4,970,313 | A | | 11/1990 | Wess et al. |
| 4,977,279 | A | | 12/1990 | Wess et al. |
| 5,260,440 | A | | 11/1993 | Hirai et al. |
| 5,273,995 | A | | 12/1993 | Roth |
| 5,354,772 | A | | 10/1994 | Kathawala |
| 5,753,675 | A | | 5/1998 | Wattanasin |
| 5,763,675 | A | | 6/1998 | Levin |
| 5,856,336 | A | | 1/1999 | Fujikawa et al. |
| 6,316,460 | B1 | | 11/2001 | Creekmore et al. |
| 6,627,636 | B2 | | 9/2003 | Robl |
| 6,835,838 | B2 | | 12/2004 | Chen et al. |
| 6,841,554 | B2 | | 1/2005 | Taylor et al. |
| 6,844,437 | B1 | | 1/2005 | Taylor et al. |
| 6,875,867 | B2 | | 4/2005 | Brodfuehrer et al. |
| 7,312,329 | B2 | | 12/2007 | Joshi et al. |
| 7,371,865 | B2 | | 5/2008 | Acemoglu et al. |
| 8,404,841 | B2 | | 3/2013 | Reddy et al. |
| 8,455,640 | B2 | | 6/2013 | Reddy et al. |
| 2004/0049036 | A1 | | 3/2004 | Taylor et al. |
| 2004/0176401 | A1 | | 9/2004 | Matsushita et al. |
| 2005/0080134 | A1 | | 4/2005 | Niddam-Hildesheim et al. |
| 2005/0124639 | A1 | | 6/2005 | Joshi et al. |
| 2005/0209259 | A1 | | 9/2005 | Huang |
| 2006/0004200 | A1 | | 1/2006 | Gudipati et al. |
| 2009/0275752 | A1 | | 11/2009 | Reddy et al. |
| 2010/0056783 | A1 | * | 3/2010 | Satyanarayana Reddy et al. ............................... 544/297 |
| 2012/0016129 | A1 | | 1/2012 | Satyanarayana Reddy et al. |

FOREIGN PATENT DOCUMENTS

| CH | 101386592 A | 3/2009 |
| CN | 1821242 A | 8/2006 |
| EP | 0 304 063 B1 | 11/1994 |
| EP | 1 099 694 B1 | 8/2005 |
| JP | 6041114 A | 5/1994 |
| WO | WO 95/11898 | 5/1995 |
| WO | WO 95/13283 | 5/1995 |
| WO | WO 97/19917 | 6/1997 |
| WO | WO 98/32751 | 7/1998 |
| WO | WO 99/11258 | 3/1999 |
| WO | WO 99/45003 | 9/1999 |
| WO | WO 01/60804 A1 | 8/2001 |
| WO | WO 02/09697 A1 | 2/2002 |
| WO | WO 02/092570 A1 | 11/2002 |
| WO | WO 02/094804 A1 | 11/2002 |
| WO | WO 03/006439 A1 | 1/2003 |
| WO | WO 03/016317 A1 | 2/2003 |
| WO | WO 03/045935 A1 | 6/2003 |

(Continued)

OTHER PUBLICATIONS

International Search Report from counterpart International Application No. PCT/IN2011/000034, titled "Improved Process for the Preparation of Amide Intermediates and Their Use Thereof", dated Jul. 14, 2011.

Miyachi, N., et al., "A Novel Synthetic Method of HMG-CoA Reductase Inhibitor NK-104 via a Hydroboration-Cross Coupling Sequence", *Tetrahedron Letters*, 34(51):8267-8270 (1993).

Wess, G., et al., "Stereoselective Synthesis of HR 780 A New Highly Potent HMG-CoA Reductase Inhibitor", *Tetrahedron Letters*, 31(18):2545-2548 (1990).

Takahashi, Kyoko, et al., "Synthesis of an Artificial Hmg-CoA Reductase Inhibitor NK-104 via a Hydrosilylation-Cross-Coupling Reaction", *Bull. Chem. Soc. Jpn.*, 68:2649-2656 (1995).

Patel, D.S., et al., "Process for preparation of 2,2-dimethylbutyric acid 8-ester of [1,2,6,7,8,8a(R)-hexahydro-2(S) ,6(R)-dimethyl-1(S)-naphthylethyl]tetrahydro-4-hydroxy-2H-pyran-2-one from broth containing [1,2,6,7,8,8a(R)-hexahydro-2(S) ,6(R)dimethyl-8(S)methyl-1-oxobutoxy-1-naphthyl]-3(R) ,5

(Continued)

*Primary Examiner* — James O Wilson
*Assistant Examiner* — Ebenezer O Sackey
(74) *Attorney, Agent, or Firm* — Hamilton, Brook, Smith & Reynolds, P.C.

(57) ABSTRACT

The present invention relates to an improved process for the preparation of amide intermediates useful in the preparation of cholesterol reducing agents.

14 Claims, 4 Drawing Sheets

(56) References Cited

FOREIGN PATENT DOCUMENTS

| | | |
|---|---|---|
| WO | WO 03/070717 A1 | 8/2003 |
| WO | WO 03/097614 A2 | 11/2003 |
| WO | WO 2004/014872 A1 | 2/2004 |
| WO | WO 2004/108691 A1 | 12/2004 |
| WO | WO 2005/033083 A1 | 4/2005 |
| WO | WO 2005/040134 A1 | 5/2005 |
| WO | WO 2005/042522 A1 | 5/2005 |
| WO | WO 2005/054207 A1 | 6/2005 |
| WO | WO 2005/077916 A1 | 8/2005 |
| WO | WO 2006/035277 A2 | 4/2006 |
| WO | WO 2006/079611 A1 | 8/2006 |
| WO | WO 2006/136407 A1 | 12/2006 |
| WO | WO 2007/000121 A1 | 1/2007 |
| WO | WO 2007/040940 A1 | 4/2007 |
| WO | WO 2007/041666 A1 | 4/2007 |
| WO | WO 2007/052309 A2 | 5/2007 |
| WO | WO 2007/086082 A2 | 8/2007 |
| WO | WO 2007/086082 A3 | 8/2007 |
| WO | WO 2007/100351 A2 | 9/2007 |
| WO | WO 2007/125547 A2 | 11/2007 |
| WO | WO 2007/125547 A3 | 11/2007 |
| WO | WO 2007/132482 A2 | 11/2007 |
| WO | WO 2007/132482 A3 | 11/2007 |
| WO | WO 2008/044243 A2 | 4/2008 |
| WO | WO 2008/044243 A3 | 4/2008 |
| WO | WO 2010/023678 A1 | 3/2010 |
| WO | WO 2011/086584 A2 | 7/2011 |

OTHER PUBLICATIONS (R)dihydroxyheptanoic acid", (abstract) Database CA [Online] Chemcial Abstracts Service Columbus, Ohio, US; Retrieved from STN International, Columbus, Ohio, USA. Accession No. 148:403004 RN 1015249-88-3 (2007).

Author unknown, "Process for the preparation of 2, 2-dimethyl-1, 2, 3, 7, 8, 8a-hexahydro-3, 7-dimethyl-8-[2-tetrahydro-4-hydroxy-6-oxo-2H-pyran-2-yl)-ethyl]-1-napthalenyl ester and intermediates thereof", *IP.com Journal*, vol. 6(10A), 2 (No. IPCOM000140631D) compounds of formula IV (Sep. 17, 2006).

Brousseau, M.E., et al., "Structure and mechanism of action of HMG-CoA reductase inhibitors", The British Library—"The World's Knowledge", pp. 19-34, ed. by Gerd Schmitz and Michael Torzewski, Birkhauser (2002).

Johnson, Douglas S., "The Art of Drug Synthesis", *Synthesis of Pitavastatin (Livalo®)*, pp. 177-179, ISBN: 15978-0-471-75215-8 (2007).

Cai, Zheng-yan et al., "Synthesis of Pitavastatin Calcium", Chinese Journal of Pharmaceuticals, 38(3): 177-182 (2007).

Minami, T., et al., "Stereoselective Reduction of β-δ-Diketo Esters Derived from Tartaric Acid. A Facile Route to Optically Active 6-OXO-3,5-syn-Isopropylidenedioxyhexanoate, a Versatile Synthetic Intermediate of Articicial HMG Co-A Reductase Inhibitors", Tetrahedron Letters, 34(3):513-516 (1993).

International Preliminary Report on Patentability for International Application No. PCT/IN2011/000034 dated Jul. 24, 2012, "Improved Process for the Preparation of Amide Intermediates and Their Use Thereof".

Written Opinion of the International Searching Authority for International Application No. PCT/IN2011/000034, "Improved Process for the Preparation of Amide Intermediates and Their Use Thereof", dated Jun. 12, 2011.

International Preliminary Report on Patentability, International Application No. PCT/IN2011/000034, Title: Process for the Preparation of Amide Intermediates and Their Use Thereof, date of issuance Jul. 24, 2012.

Written Opinion, International Application No. PCT/IN2011/000034, Title: Process for the Preparation of Amide Intermediates and Their Use Thereof, date of mailing Jul. 14, 2011.

\* cited by examiner

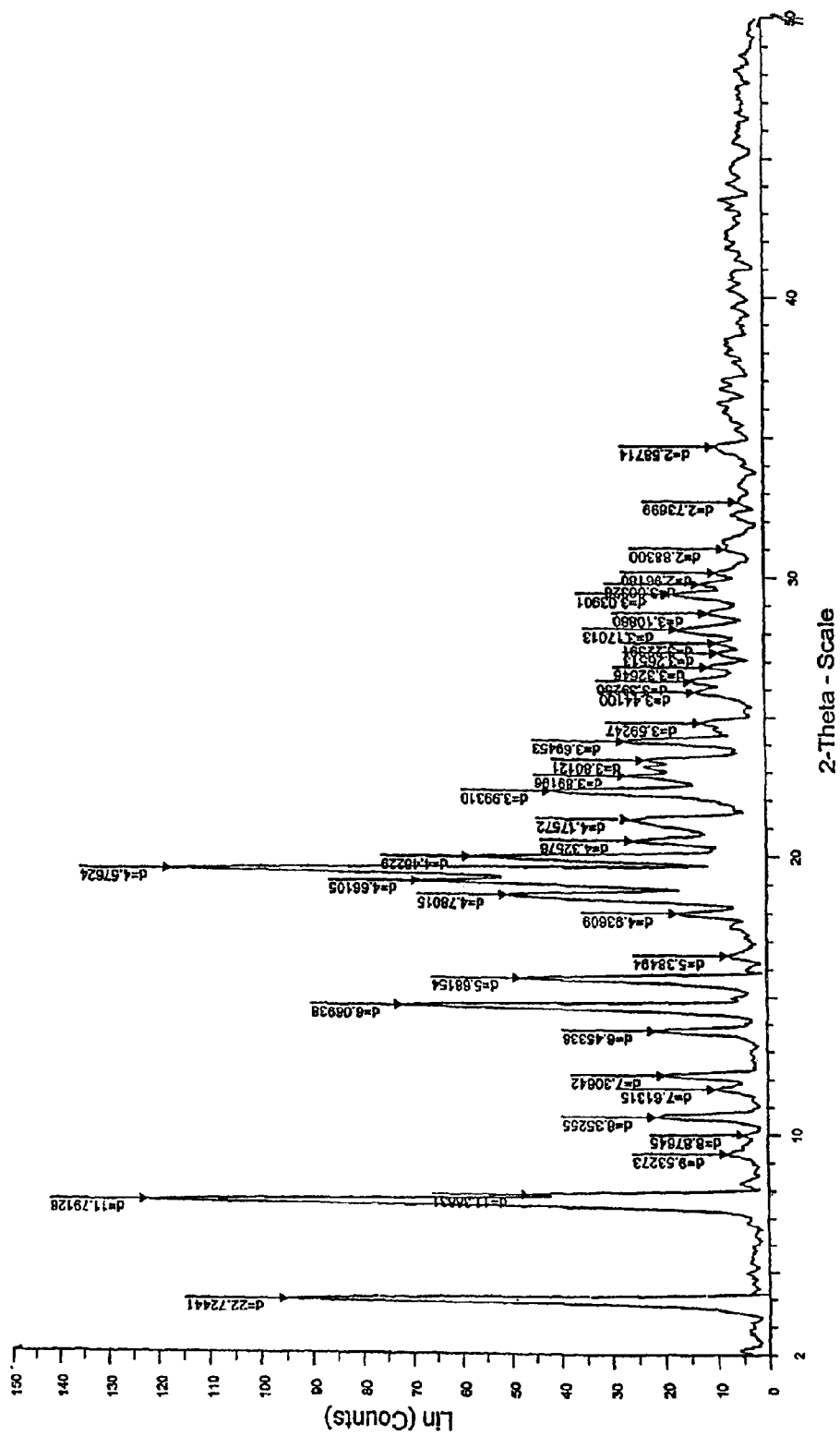

PROCESS FOR THE PREPARATION OF AMIDE INTERMEDIATES AND THEIR USE THEREOF

RELATED APPLICATION

This application is the U.S. National Stage of International Application No. PCT/IN2011/000034, filed Jan. 17, 2011, which designates the U.S., published in English, and claims priority under 35 U.S.C. §§119 or 365(c) to Indian Application No. 124/CHE/2010, filed Jan. 18, 2010 and Indian Application No. 515/CHE/2010 filed Mar. 1, 2010. The entire teachings of the above applications are incorporated herein by reference.

FIELD OF THE INVENTION

The present invention relates to an improved process for the preparation of 2-((4R,6S)-6-((E)-2-(4-(4-fluorophenyl)-6-isopropyl-2-(N-methylmethylsulfonamido) pyrimidin-5-yl)vinyl)-2,2-dimethyl-1,3-dioxan-4-yl)-N,N-disubstitutedacetamides compound of general formula-1 and N-butyl-2-((4R,6S)-6-formyl-2,2-dimethyl-1,3-dioxan-4-yl) acetamide.

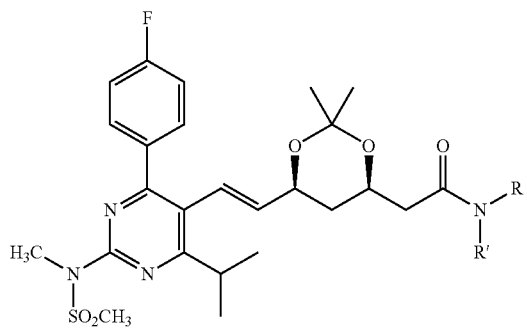

Formula-1 wherein R and R' is independently selected from hydrogen, alkyl, aryl or aralkyl.

The present invention also relates to novel crystalline forms of formula-1a (wherein R is n-butyl and R' is H). The compounds of general formula-1 are important intermediates in the preparation of rosuvastatin, a member of drug class of statins (HMG-CoA reductase inhibitors), used to treat high cholesterol and related conditions, and to prevent cardiovascular disease.

BACKGROUND OF THE INVENTION

The compounds of general formula-1 and its use in the preparation of rosuvastatin was first disclosed in WO 2008/44243. The disclosed process involves the condensation of N-(4-(4-fluorophenyl)-6-isopropyl-5-((1-methyl-1H-benzo [d]imidazol-2-ylsulfonyl) methyl)pyrimidin-2-yl)-N-methylmethanesulfonamide with N-butyl-2-((4R,6S)-6-formyl-2,2-dimethyl-1,3-dioxan-4-yl)acetamide and the condensed intermediate was hydrolyzed followed by treatment with calcium ion source to provide the rosuvastatin calcium. The said process is having disadvantage of formation of high levels of unwanted Z isomer up to 5% along with required E isomer. Hence there is a need in the art for an improved process which able to control the formation of the unwanted isomer.

N-butyl-2-((4R,6S)-6-formyl-2,2-dimethyl-1,3-dioxan-4-yl)acetamide and its use in the in the preparation of statin compounds (HMG-CoA reductase inhibitors) was also disclosed in PCT publication number WO 2008/044243. The said publication disclosed different processes for the preparation of the same.

Statin compounds such as rosuvastatin, pitavastatin, fluvastatin, atorvastatin, simvastatin and lovastatin are important drugs used for treatment of cholesterol reduction. Hence it is advantageous to have a novel and efficient process for the preparation of important intermediate like N-butyl-2-((4R, 6S)-6-formyl-2,2-dimethyl-1,3-dioxan-4-yl)acetamide, so that it can be used effectively in the preparation of statin compounds.

There is always need to improve the process efficiency for the preparation of important drugs. Hence the main objective of the present invention is to provide an improved process for the preparation of compound of formula-1 which controls the formation of unwanted isomer and also provides the novel crystalline forms of compound of formula-1a and its use. And also to provide novel and efficient process for the preparation of N-butyl-2-((4R,6S)-6-formyl-2,2-dimethyl-1,3-dioxan-4-yl)acetamide, which is more effective and easy to scale up to commercial level in a convenient and cost effective manner.

BRIEF DESCRIPTION OF THE INVENTION

The first aspect of the present invention is to provide an improved process for the preparation of 2-((4R,6S)-6-((E)-2-(4-(4-fluorophenyl)-6-isopropyl-2-(N-methylmethylsulfonamido)pyrimidin-5-yl)vinyl)-2,2-dimethyl-1,3-dioxan-4-yl)-N,N-disubstitutedacetamide compounds of general formula-1 containing low levels of unwanted Z-isomer, which comprises of reacting the N-(4-(4-fluorophenyl)-6-isopropyl-5((1-methyl-1H-benzo[d]imidazol-2-ylsulfonyl) methyl)pyrimidin-2-yl)-N-methyl methane sulfonamide compound of formula-2 with aldehyde compound of formula-3 in the presence of a suitable alkali metal alkoxide base in a suitable solvent to provide the compound of formula-1.

The second aspect of the present invention is to provide an improved process for the preparation of rosuvastatin calcium compound of formula-4, which comprises of the following steps a) Treating the N-butyl-2-((4R,6S)-6-((E)-2-(4-(4-fluorophenyl)-6-isopropyl-2-(N-methylmethylsulfonamido)pyrimidin-5-yl)vinyl)-2,2-dimethyl-1,3-dioxan-4-yl)acetamide compound of formula-1a with suitable organic acid in a suitable solvent to provide the dihydroxy compound of formula-5, b) optionally purifying the compound of formula-5 using suitable solvent to provide highly pure compound of formula-5, c), hydrolyzing the compound of formula-5 with a suitable base in a suitable solvent provides the corresponding salt of rosuvastatin, which on in-situ treatment with a suitable calcium source provides the rosuvastatin calcium compound of formula-4.

The third aspect of the present invention is to provide novel crystalline forms namely form I, form II & form III of N-butyl-2-((4R,6S)-6-((E)-2-(4-(4-fluorophenyl)-6-isopropyl-2-(N-methylmethylsulfonamido)pyrimidin-5-yl)vinyl)-2,2-dimethyl-1,3-dioxan-4-yl)acetamide compound of formula-1a, process for their preparation and use.

The fourth aspect of the present invention is to provide a novel crystalline form of (3R,5S,E)-N-butyl-7-(4-(4-fluorophenyl)-6-isopropyl-2-(N-methylmethyl sulfonamido)

pyrimidin-5-yl)-3,5-dihydroxyhept-6-enamide compound of formula-5, process for its preparation and its use.

The fifth aspect of the present invention is to provide a process for the preparation of N-butyl-2-((4R,6S)-6-formyl-2,2-dimethyl-1,3-dioxan-4-yl)acetamide compound of formula-3a, which comprises of the following steps;
a) Reacting the tert-butyl 2-((4R,6S)-6-(hydroxymethyl)-2,2-dimethyl-1,3-dioxan-4-yl)acetate compound of formula-6 with n-butyl amine in methanol in the presence or absence of a suitable base, to provide the N-butyl-2-((4R,6S)-6-(hydroxymethyl)-2,2-dimethyl-1,3-dioxan-4-yl)acetamide compound of formula-9,
b) oxidizing the compound of formula-9 with a suitable oxidizing agent in presence of a catalyst in a suitable solvent to provide the compound of formula-3a.

Synthesis of N-butyl-2-((4R,6S)-6-formyl-2,2-dimethyl-1,3-dioxan-4-yl)acetamide compound of formula-3a was also carried out without the isolation of step a) product i.e. compound of formula-9 and oxidizing it in-situ with a suitable oxidizing agent and a solvent to provide the compound of formula-3a.

The sixth aspect of the present invention is to provide a novel process for the preparation of N-butyl-2-((4R,6S)-6-formyl-2,2-dimethyl-1,3-dioxan-4-yl)acetamide compound of formula-3a, which comprises of the following steps:
a) Hydrolyzing the tert-butyl 2-((4R,6S)-6-(hydroxymethyl)-2,2-dimethyl-1,3-dioxan-4-yl)acetate compound of formula-6 with a suitable base in a suitable solvent provides the 2-((4R,6S)-6-(hydroxymethyl)-2,2-dimethyl-1,3-dioxan-4-yl)acetic acid compound of formula-7,
b) treating the compound of formula-7 with dimethylsulfate in the presence of a suitable base in methanol to provide methyl 2-((4R,6S)-6-(hydroxy methyl)-2,2-dimethyl-1,3-dioxan-4-yl)acetate compound of formula-8,
c) reacting the compound of formula-8 with n-butyl amine in the presence or absence of a base and solvent, provides the N-butyl-2-((4R,6S)-6-(hydroxymethyl)-2,2-dimethyl-1,3-dioxan-4-yl)acetamide compound of formula-9,
d) oxidizing the compound of formula-9 with a suitable oxidizing agent in the presence of a catalyst in a suitable solvent to provide the N-butyl-2-((4R,6S)-6-formyl-2,2-dimethyl-1,3-dioxan-4-yl)acetamide compound of formula-3a.

The seventh aspect of the present invention is to provide another process for the preparation of compound of formula-3a, which comprises of the following steps;
a) Reacting the ethyl 2-((4R,6S)-6-(acetoxymethyl)-2,2-dimethyl-1,3-dioxan-4-yl)acetate compound of formula-10 with a suitable base in methanol to provide the methyl 2-((4R,6S)-6-(hydroxymethyl)-2,2-dimethyl-1,3-dioxan-4-yl)acetate compound of formula-8,
b) reacting the compound of formula-8 with n-butyl amine in the presence or absence of a solvent to provide the N-butyl-2-((4R,6S)-6-(hydroxymethyl)-2,2-dimethyl-1,3-dioxan-4-yl)acetamide compound of formula-9,
c) oxidizing the compound of formula-9 with a suitable oxidizing agent in the presence of a catalyst in a suitable solvent to provide the N-butyl-2-((4R,6S)-6-formyl-2,2-dimethyl-1,3-dioxan-4-yl)acetamide compound of formula-3a.

Further aspect of the present invention is to provide a process for the preparation of ethyl 2-((4R,6S)-6-(acetoxymethyl)-2,2-dimethyl-1,3-dioxan-4-yl)acetate compound of formula-10, which comprises of the following steps:
a) Reacting the (S)-4-chloro-3-(trimethylsilyloxy)butanenitrile compound of formula-11 with ethyl bromo acetate compound of formula-12 in presence of zinc dust and a suitable acid in a suitable solvent to provide the (S)-ethyl 6-chloro-5-hydroxy-3-oxohexanoate compound of formula-13,
b) reducing the compound of formula-13 by treating it with diethyl methoxy, borane in the presence of a suitable reducing agent in a suitable solvent to provide the (3R,5S)-ethyl 6-chloro-3,5-dihydroxyhexanoate compound of formula-14,
c) treating the (3R,5S)-ethyl 6-chloro-3,5-dihydroxyhexanoate compound of formula-14 with 2,2-dimethoxy propane in the presence of an acid in a suitable solvent to provide the ethyl 2-((4R,6S)-6-(chloromethyl)-2,2-dimethyl-1,3-dioxan-4-yl)acetate compound of formula-15,
d) reacting the compound of formula-15 with sodium acetate in presence of a phase transfer catalyst in a suitable solvent to provide the ethyl 2-((4R,6S)-6-(acetoxymethyl)-2,2-dimethyl-1,3-dioxan-4-yl)acetate, compound of formula-10.

DETAILED DESCRIPTION OF THE INVENTION

Figure 1:
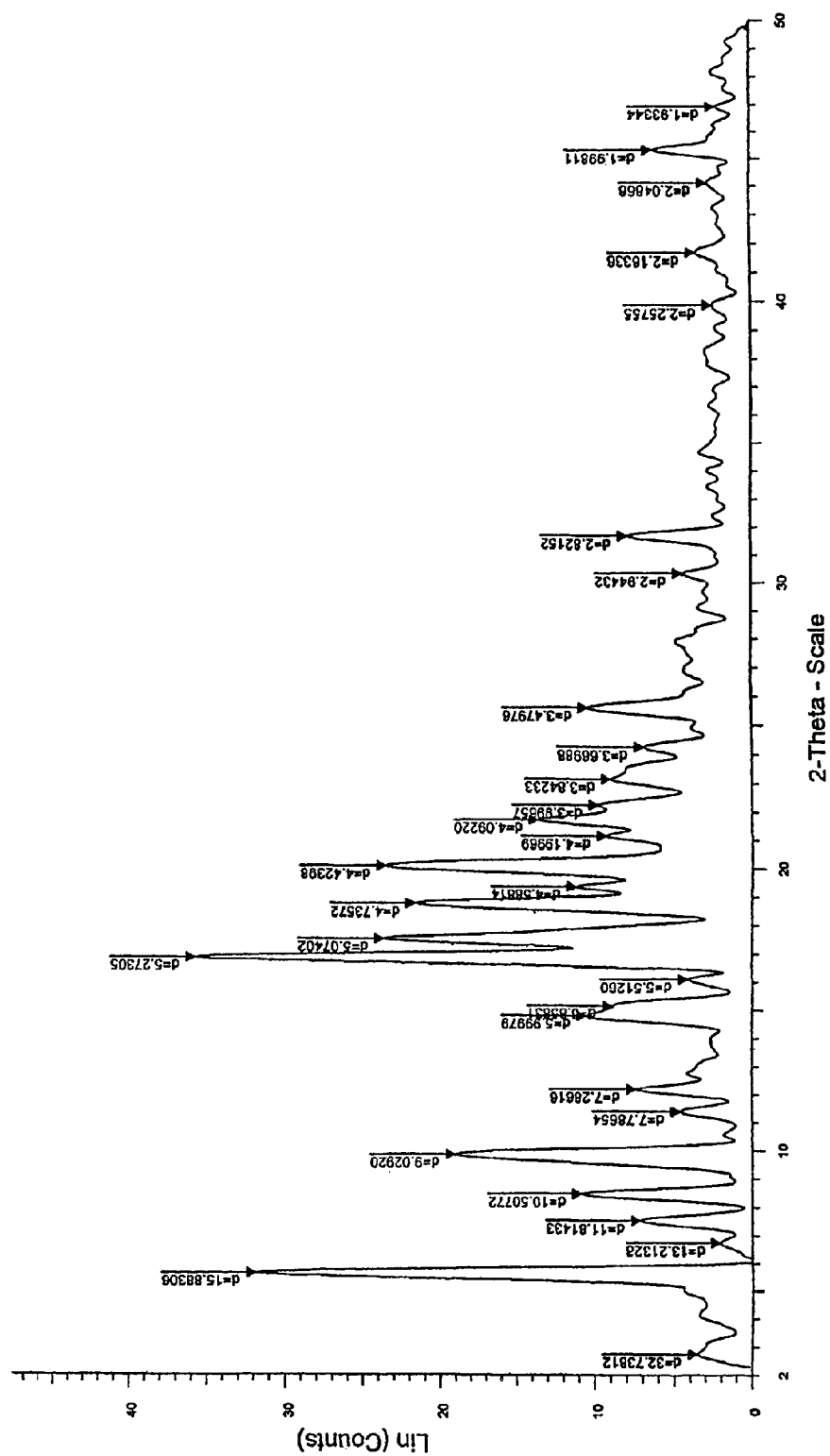
FIG. 1: Illustrates the powder X-ray diffractogram of crystalline form-I of formula-1a
FIG. 2: Illustrates the powder X-ray diffractogram of crystalline form-II of formula-1a
FIG. 3: Illustrates the powder X-ray diffractogram of crystalline form-III of formula-1a
FIG. 4: Illustrates the powder X-ray diffractogram of crystalline form of (3R,5S,E)-N-butyl-7-(4-(4-fluorophenyl)-6-isopropyl-2-(N-methylmethyl sulfonamido) pyrimidin-5-yl)-3,5-dihydroxyhept-6-enamide compound of formula-5.
Figure 2:
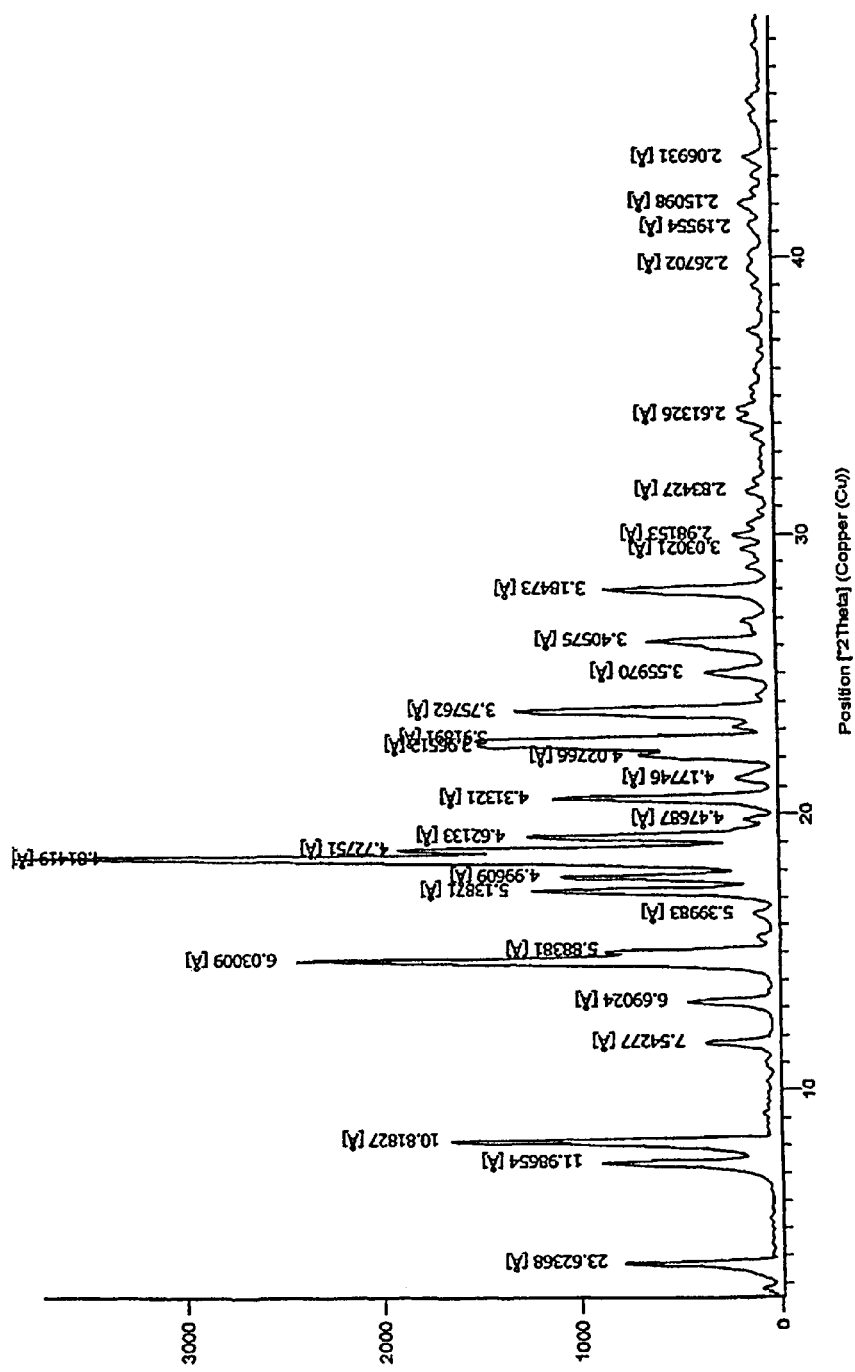
Figure 3:
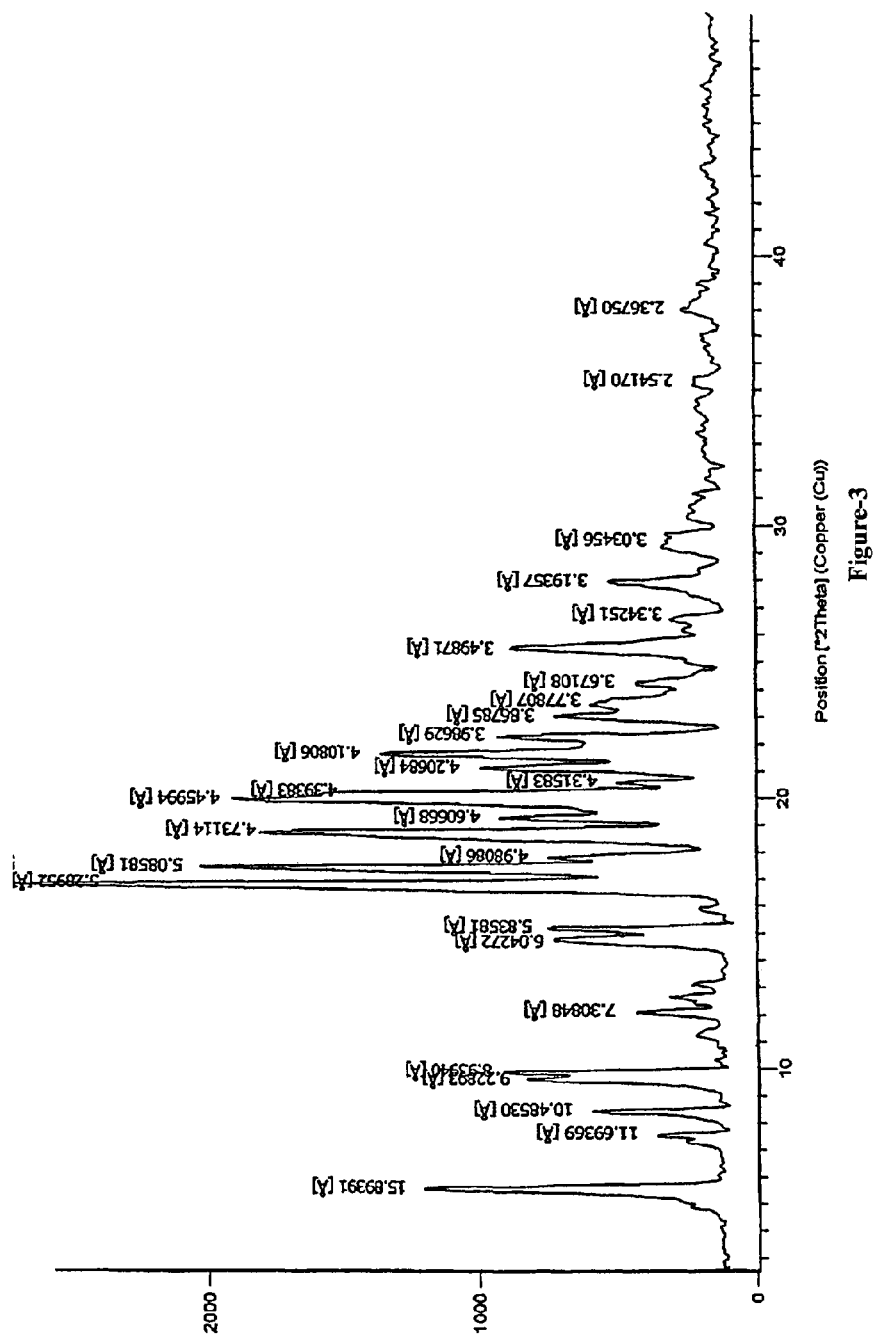

As used herein the present invention, the term "suitable solvent" refers to the solvent selected from "polar solvents" such as water; "polar aprotic solvents" such as dimethylsulfoxide, dimethylacetamide, dimethyl formamide and the like; "nitrile solvents" such as acetonitrile, propionitrile, butyronitrile and isobutyronitrile and the like; "ether solvents" such as di-tert-butylether, diethylether, diisopropyl ether, 1,4-dioxane, methyltert-butylether, ethyl tert-butyl ether, tetrahydrofuran and dimethoxyethane; "alcohol solvents" such as methanol, ethanol, n-propanol, isopropanol and n-butanol and the like; "chloro solvents" such as methylene chloride, ethylene dichloride, carbon tetra chloride, chloroform and the like; "hydrocarbon solvents" such as benzene, toluene, xylene, heptane, hexane and cyclohexane; "ketone solvents" such as acetone, ethyl methyl ketone, diethyl ketone, methyl tert-butyl ketone, isopropyl ketone and the like; "esters solvents" such as ethyl acetate, methyl acetate, n-butyl acetate, isobutyl acetate, sec-butyl acetate, isopropyl acetate and the like; and their mixtures thereof.

As used herein the term "alkyl" refers to a straight or branched or cyclic $C_1$ to $C_6$ alkyl, including methyl, ethyl, n-propyl, isopropyl, cyclopropyl, n-butyl, isobutyl, sec-butyl, tert-butyl, cyclobutyl, n-pentyl, isopentyl, neopentyl, tert-pentyl, cyclopentyl, n-hexyl, and isohexyl and the like. Further, the alkyl may be substituted by 1 to 3 substituents independently selected from the group consisting of halogen, amino, hydroxy and cyano. Halogen means fluorine, chlorine, bromine and iodine.

As used herein the term "aryl" refers to $C_6$-$C_{12}$ aromatic group include phenyl, tolyl, xylyl, biphenyl, naphthyl and the like. The aryl may have 1 to 3 substituents independently selected from the group consisting of lower alkyl, halogen, amino, cyano, hydroxy.

As used herein the term "aralkyl" refers to $C_1$-$C_6$ lower alkyl substituted by $C_6$-$C_{12}$ aromatic aryl group defined above. For example are benzyl, phenylethyl, phenylpropyl and the like each of which may have 1 to 3 substituents independently selected from the group consisting of alkyl, halogen, amino, cyano, hydroxy and the like.

As used herein present invention the term "suitable base" refers to the bases selected from "alkali metal hydroxides" such as sodium hydroxide, potassium hydroxide and the like; "alkali metal carbonates" such as sodium carbonate, potassium carbonate, cesium carbonate and the like; "alkali metal bicarbonates" such as sodium bicarbonate, potassium bicarbonate and the like; "alkali metal alkoxide" such as sodium methoxide, potassium methoxide, sodium tertiary butoxide and potassium tertiary butoxide and the like;

The term "statins" used herein the present invention refers to the HMG-CoA reductase inhibitors like rosuvastatin, pitavastatin, fluvastatin, atorvastatin, simvastatin, lovastatin and other dihydroxy acid HMG-CoA reductase inhibitors.

Accordingly, the first aspect of the invention provides a process for the preparation of 2-((4R,6S)-6-((E)-2-(4-(4-fluorophenyl)-6-isopropyl-2-(N-methylmethyl sulfonamido) pyrimidin-5-yl)vinyl)-2,2-dimethyl-1,3-dioxan-4-yl)-N,N-disubstituted acetamide compounds of general formula-1 containing low levels of unwanted Z-isomer, Formula-1

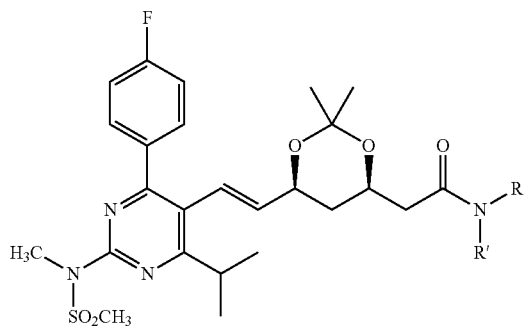

wherein R and R' is independently selected from hydrogen, alkyl, aryl or aralkyl.

which comprises of reacting the N-(4-(4-fluorophenyl)-6-isopropyl-5((1-methyl-1H-benzo[d]imidazol-2-ylsulfonyl) methyl)pyrimidin-2-yl)-N-methylmethanesulfonamide compound of formula-2

Formula-2

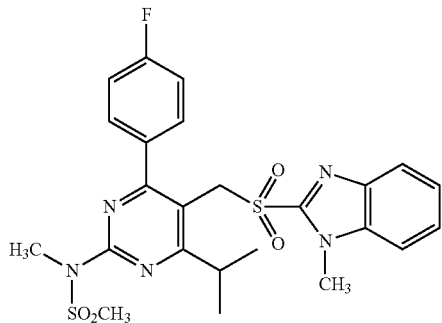

with aldehyde compounds of general formula-3

Formula-3

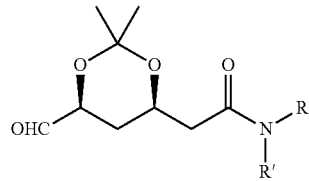

wherein R and R' is independently selected from hydrogen, alkyl, aryl or aralkyl.

in the presence of a suitable alkali metal alkoxide base selected from sodium methoxide, potassium methoxide, sodium tertiary butoxide, potassium tertiary butoxide, or mixtures thereof in a suitable solvent selected from polar aprotic solvents, alcohol solvents, hydrocarbon solvents, polar solvents, ether solvents or mixtures thereof to provide the compounds of general formula-1.

According to the present invention the alkali metal alkoxide base used in the ratio of 0.8 to 2.5 moles with respect to N-(4-(4-fluorophenyl)-6-isopropyl-5((1-methyl-1H-benzo [d]imidazol-2-ylsulfonyl)methyl)pyrimidin-2-yl)-N-methylmethanesulfonamide compound of formula-2 and the condensation reaction is carried out at −30° C. to 70° C., preferably at −20 to 25° C.

The compound of formula-1 prepared as per the process disclosed in WO 2007/125547 via Julia olefination having E/Z isomer content in the ratio of 95:5. Even though the process reduces the Z isomer content over the prior art, still its content is considerably high as the condensation reaction takes place in presence of potassium carbonate at 70-75° C., it leads to the degradation of starting material and decrease in the yields and purity. The same has been avoided in the preparation of compound of formula-1 by the present invention, by replacing the potassium carbonate with alkali metal alkoxide and carrying out the reaction at lower temperature, which avoids the degradation of starting material and provides the final compound with high purity and low Z isomer content. It is possible to bring down the Z isomer content to less than 0.1% with the usage of alkoxide base.

The compound of formula-1 prepared as per the present invention is having the E/Z isomer content in the ratio 97:3, preferably 99:1; more preferably 99.9:0.1. When the same compound of formula-1 used in the preparation of rosuvastatin or its pharmaceutically acceptable salts, it provided the product containing low levels of unwanted isomer (Z isomer) i.e., E/Z isomer are in the ratio of 99:1 and preferably 99.9:0.1. Hence the process provides product with higher purity and greater yields.

In a preferred embodiment, the present invention provides a process for the preparation of N-butyl-2-((4R,6S)-6-((E)-2-(4-(4-fluorophenyl)-6-isopropyl-2-(N-methyl methylsulfonamido)pyrimidin-5-yl)vinyl)-2,2-dimethyl-1,3-dioxan-4-yl)acetamide compound of formula-1a, Formula-1a

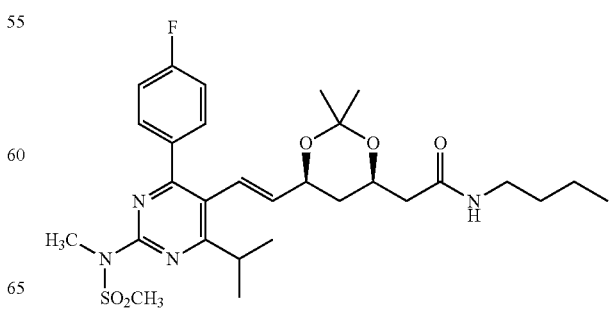

which comprise of reacting the N-(4-(4-fluorophenyl)-6-isopropyl-5((1-methyl-1H-benzo[d]imidazol-2-ylsulfonyl)methyl)pyrimidin-2-yl)-N-methylmethanesulfonamide compound of formula-2 with N-butyl-2-((4R,6S)-6-formyl-2,2-dimethyl-1,3-dioxan-4-yl)acetamide compound of formula-3a Formula-3a

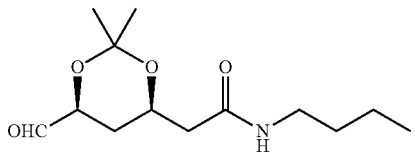

in the presence of sodium or potassium tertiary butoxide, preferably sodium tertiary butoxide in tetrahydrofuran to provide the compound of formula-1a.

The second aspect of the present invention provides an improved process for the preparation of rosuvastatin calcium compound of formula-4

Formula-4

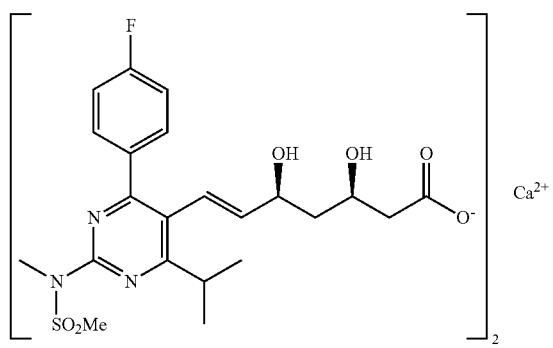

which comprises of the following steps;
a) Treating the N-butyl-2-((4R,6S)-6-((E)-2-(4-(4-fluorophenyl)-6-isopropyl-2-(N-methylmethylsulfonamido)pyrimidin-5-yl)vinyl)-2,2-dimethyl-1,3-dioxan-4-yl)acetamide compound of formula-1a with suitable organic acid such as oxalic acid in a suitable alcoholic solvent like methanol, ethanol, isopropanol, butanol or nitrile solvents like acetonitrile or mixtures thereof, preferably methanol to provide the dihydroxy compound of formula-5, Formula-5

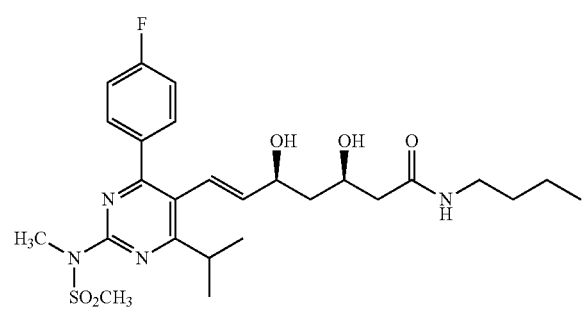

b) optionally purifying the compound of formula-5 using suitable solvent selected from aromatic hydrocarbon solvent like toluene, heptane, hexane or cyclohexane; nitrile solvent like acetonitrile or mixtures thereof provides the highly pure compound of formula-5,
c) hydrolyzing the compound of formula-5 with suitable alkali metal hydroxide base like sodium hydroxide in a suitable alcoholic solvent like isopropyl alcohol provides the rosuvastatin sodium, which on in-situ treatment with aqueous calcium acetate solution provides the rosuvastatin calcium compound of formula-4.

The third aspect of the present invention provides novel crystalline forms of N-butyl-2-((4R,6S)-6-((E)-2-(4-(4-fluorophenyl)-6-isopropyl-2-(N-methylmethyl sulfonamido)pyrimidin-5-yl)vinyl)-2,2-dimethyl-1,3-dioxan-4-yl)acetamide compound of formula-1a. The novel crystalline forms of formula-1a of the present invention are herein designated as Form-I, Form-II and Form-III.

The novel crystalline form I of formula-1a of the present invention is characterized by its powder X-ray diffractogram having peaks at about 5.56, 7.47, 8.40, 9.78, 14.75, 16.80, 17.46, 18.72, 20.05, 21.13, 21.70, 23.13, 25.57, 31.68 & 45.35±0.2 degrees 2θ.

The novel crystalline form II of formula-1a of the present invention is characterized by its powder X-ray diffractogram peaks at about 3.74, 7.37, 8.17, 14.69, 15.05, 17.25, 17.75, 18.42, 18.77, 19.20, 20.59, 22.42, 22.69, 23.67 & 28.01±0.2 degrees 2θ.

The novel crystalline form III of formula-1a of the present invention is characterized by its powder X-ray diffractogram having peaks at about 8.43, 9.58, 9.89, 14.65, 15.18, 16.76, 17.43, 18.75, 19.26, 19.90, 20.21, 21.11, 21.63, 22.30, 25.45 & 27.93±0.2 degrees 2θ.

The novel crystalline form I, II and III of formula-1a of the present invention are used to prepare highly pure rosuvastatin, its pharmaceutically acceptable salts and its intermediate such as formula-5.

Further the present invention provides a process for the preparation of crystalline form I of formula-1a, which comprises of following steps;
a) dissolving the compound of formula-1a in a suitable hydrocarbon solvent,
b) concentrating the reaction mixture followed by co-distillation with cyclohexane,
c) adding suitable ether or alcohol solvent to the obtained residue,
d) stirring the reaction mixture,
e) filtering the solid and washing with suitable ether or alcohol solvent.
f) drying the solid to get the crystalline form I of formula-1a.
In a preferred embodiment, a process for the preparation of crystalline form I of formula-1a comprises of the following steps;
a) dissolving the compound of formula-1a in toluene,
b) concentrating the reaction mixture followed by co-distillation with cyclohexane,
c) adding diisopropylether to the residue,
d) stirring the reaction mixture,
e) filtering the solid and washing with diisopropylether,
f) drying the solid to get the crystalline form I of formula-1a.

The present invention also provides a process for the preparation of crystalline form II of formula-1a, which comprises of the following steps,
a) dissolving the compound of formula-1a in suitable hydrocarbon solvent,
b) concentrating the reaction mixture followed by co-distillation with cyclohexane,
c) adding cyclohexane to the residue,
d) stirring the reaction mixture, e) filtering the solid and washing with cyclohexane,
f) drying the solid to get the crystalline form II of formula-1a.

In a preferred embodiment, a process for the preparation of crystalline form II of formula-1a comprises of the following steps,
a) dissolving the compound of formula-1a in toluene,
b) concentrating the reaction mixture followed by co-distillation with cyclohexane,
c) adding cyclohexane to the residue,
d) stirring the reaction mixture,
e) filtering the solid and washing with cyclohexane,
f) drying the solid to get the crystalline form II of formula-1a.

Further the present invention provides a process for the preparation of crystalline form III of formula-1a, which comprises of the following steps;
a) dissolving the compound of formula-1a in a suitable alcohol solvent,
b) adding water to the above solution,
c) filtering the solid and washing with water,
d) drying the solid to get the crystalline form III of formula-1a.

In a preferred embodiment, a process for the preparation of crystalline form III of formula-1a comprises of the following steps;
a) dissolving the compound of formula-1a in methanol,
b) adding water to the above solution,
c) filtering the solid and washing with water,
d) drying the solid to get the crystalline form III of formula-1a.

The fourth aspect of the present invention provides a novel crystalline form of (3R,5S,E)-N-butyl-7-(4-(4-fluorophenyl)-6-isopropyl-2-(N-methylmethylsulfonamido) pyrimidin-5-yl)-3,5-dihydroxyhept-6-enamide compound of formula-5

Formula-5

The novel crystalline form of formula-5 of the present invention is characterized by its powder X-ray diffractogram peaks at about 3.88, 7.49, 7.75, 9.27, 10.58, 14.58, 15.58, 18.54, 19.02, 19.38, 19.88, 22.24, 24.06 & 28.12±0.2 degrees 2θ.

The novel crystalline form of formula-5 of the present invention is used to prepare highly pure rosuvastatin and its pharmaceutically acceptable salts.

The present invention further provides a process for the preparation of novel crystalline form of formula-5 of the present invention, which comprises of the following steps;
a) Dissolving the compound of formula-5 in a suitable hydrocarbon solvent by heating to reflux temperature,
b) cooling the reaction mixture and stirring the reaction mixture,
c) filtering the solid and washing with suitable hydrocarbon solvent,
d) dissolving the obtained solid in a suitable solvent selected from hydrocarbon solvent, nitrile solvent or mixture thereof at reflux temperature,
e) cooling the reaction mixture and stirring,
f) filtering the solid and washing with hydrocarbon solvent,
g) drying the solid to get the crystalline form of formula-5.

In a preferred embodiment, process for the preparation of novel crystalline form of formula-5 comprises of the following steps,
a) Dissolving the compound of formula-5 in toluene by heating to reflux temperature,
b) cooling the reaction mixture to 0-5° C. and stirring the reaction mixture,
c) filtering the solid and washing with toluene,
d) dissolving the obtained solid in a mixture of toluene and acetonitrile at reflux temperature,
e) cooling the reaction mixture and stirring,
f) filtering the solid and washing with toluene,
g) drying the solid to get the crystalline form of formula-5.

The present invention is schematically represented by the following scheme.

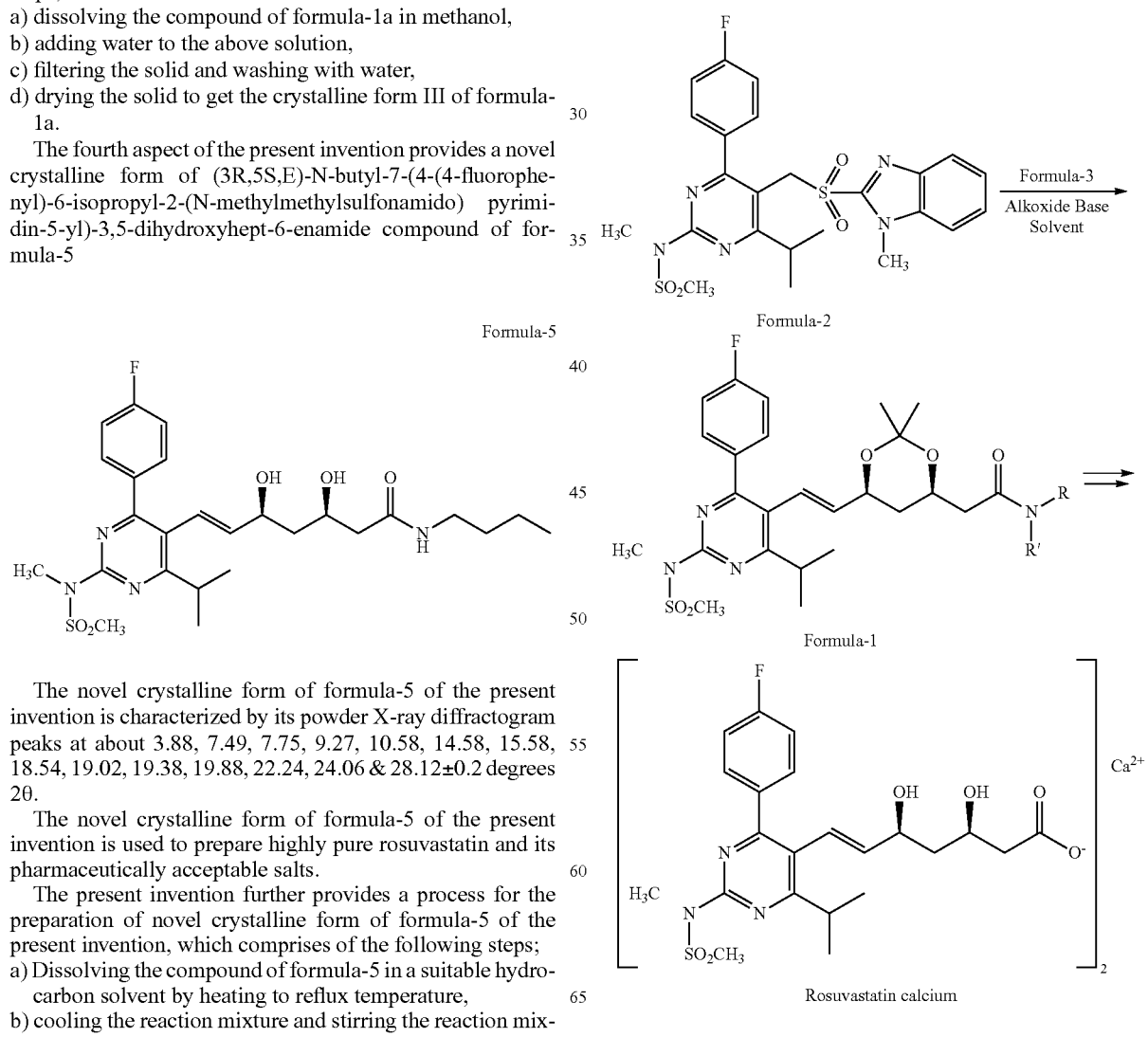

The fifth aspect of the present invention provides a process for the preparation of N-butyl-2-((4R,6S)-6-formyl-2,2-dimethyl-1,3-dioxan-4-yl)acetamide compound of formula-3a,

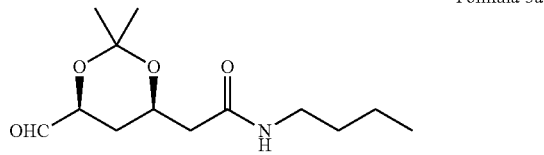

Formula-3a which comprises of the following steps;
a) Reacting the tert-butyl 2-((4R,6S)-6-(hydroxymethyl)-2,2-dimethyl-1,3-dioxan-4-yl)acetate of formula-6,

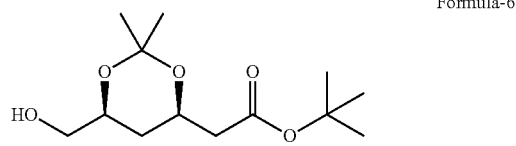

Formula-6 with n-butyl amine in methanol and in the presence or absence of a base provides the N-butyl-2-((4R,6S)-6-(hydroxymethyl)-2,2-dimethyl-1,3-dioxan-4-yl)acetamide compound of formula-9,

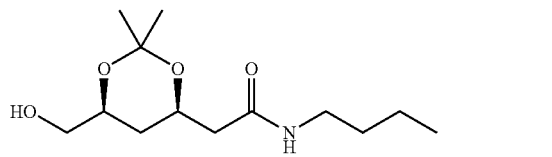

Formula-9 b) oxidizing the compound of formula-9 with suitable oxidizing agent selected from sodium hypochlorite in the presence of a catalyst like TEMPO (2,2,6,6-tetramethyl-1-piperidinyloxy, free radical)/KBr or oxalyl chloride/dimethyl sulfoxide in a suitable solvent to provide the N-butyl-2-((4R,6S)-6-formyl-2,2-dimethyl-1,3-dioxan-4-yl)acetamide compound of formula-3a.

Further the invention also provides a one pot process for the preparation of compound of formula-3a, wherein the compound of formula-9 is not isolated and further oxidized in-situ with a suitable oxidizing agent and solvent as described above to provide the compound of formula-3a.

As per the PCT publication number WO2008/044243, the N-butyl-2-((4R,6S)-6-formyl-2,2-dimethyl-1,3-dioxan-4-yl) acetamide compound of formula-3a prepared by the reaction of (3R,5S)-tert-butyl 3,5,6-trihydroxy hexanoate with n-butylamine at 70-80° C. to provide the (3R,5S)—N-butyl-3,5,6-trihydroxyhexanamide, which on further reaction with 2,2-dimethoxy propane to provide N-butyl-2-((4R,6S)-6-(hydroxymethyl)-2,2-dimethyl-1,3-dioxan-4-yl)acetamide followed by oxidation with oxalyl chloride provides the compound of formula-3a. The said process involves column chromatography purification in each stage and the amidation reaction take place without usage of solvent. When the present inventors were working on the same reaction, it was surprisingly found that the n-butyl amine reaction with protected dihydroxy compound i.e., tert-butyl 2-((4R,6S)-6-(hydroxymethyl)-2,2-dimethyl-1,3-dioxan-4-yl)acetate in presence of methanol solvent provides the compound with high purity and yield. However, it was observed that when ethanol is used in place of methanol the said reaction was not proceeded further.

In a preferred embodiment of the present invention, the process for the preparation of compound of formula-3a comprises of the following steps, a) Reacting the tert-butyl 2-((4R,6S)-6-(hydroxymethyl)-2,2-dimethyl-1,3-dioxan-4-yl)acetate compound of formula-6 with n-butyl amine in methanol and in the presence of a suitable base like alkali metal carbonates, preferably potassium carbonate to provide the N-butyl-2-((4R,6S)-6-(hydroxymethyl)-2,2-dimethyl-1,3-dioxan-4-yl)acetamide compound of formula-9, b) oxidizing the compound of formula-9 in-situ with a suitable oxidizing agent preferably with sodium hypochlorite in presence of a catalyst like TEMPO (2,2,6,6-tetramethyl-1-piperidinyloxy, free radical)/KBr in a suitable solvent preferably chloro solvents like methylene chloride to provide the N-butyl-2-((4R,6S)-6-formyl-2,2-dimethyl-1,3-dioxan-4-yl)acetamide compound of formula-3a.

Further the reaction between N-(4-(4-fluorophenyl)-6-isopropyl-5((1-methyl-1H-benzo[d]imidazol-2-ylsulfonyl)methyl)pyrimidin-2-yl)-N-methylmethanesulfonamide compound of formula-2 with n-butyl, amine of step a) also be carried out with out using any base under nitrogen condition.

Further the present invention also provides a process for the preparation of N-butyl-2-((4R,6S)-6-formyl-2,2-dimethyl-1,3-dioxan-4-yl)acetamide compound of formula-3a, which comprises of oxidizing the N-butyl-2-((4R,6S)-6-(hydroxymethyl)-2,2-dimethyl-1,3-dioxan-4-yl)acetamide compound of formula-9 with a suitable oxidizing agent preferably with sodium hypochlorite in presence of a catalyst like AZADO(Azaadamantane N-oxyl, free radical)/KBr or I-Me-AZADO/KBr in a suitable solvent preferably chloro solvents like methylene chloride provides N-butyl-2-((4R,6S)-6-formyl-2,2-dimethyl-1,3-dioxan-4-yl)acetamide compound of formula-3a.

The sixth aspect of the present invention provides a novel process for the preparation of N-butyl-2-((4R,6S)-6-formyl-2,2-dimethyl-1,3-dioxan-4-yl)acetamide compound of formula-3a, which comprise of the following steps;

a) Hydrolyzing the tert-butyl 2-((4R,6S)-6-(hydroxymethyl)-2,2-dimethyl-1,3-dioxan-4-yl)acetate compound of formula-6

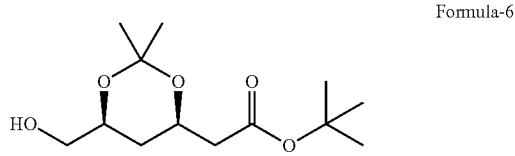 [SMILES: CC(C)(C)OC(=O)C[C@H]1C[C@@H](CO)OC(C)(C)O1]

Formula-6 with a suitable base in a suitable solvent, to provide the 2-((4R,6S)-6-(hydroxy methyl)-2,2-dimethyl-1,3-dioxan-4-yl)acetic acid compound of formula-7,

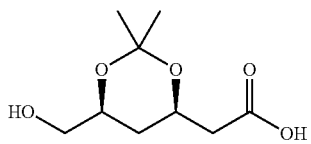

Formula-7 b) treating the compound of formula-7 with dimethylsulfate in the presence of a suitable base in a suitable solvent, to provide the methyl 2-((4R,6S)-6-(hydroxymethyl)-2,2-dimethyl-1,3-dioxan-4-yl)acetate compound of formula-8,

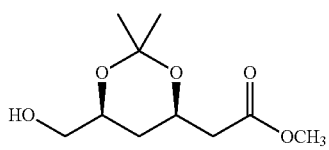

Formula-8 c) reacting the compound of formula-8 with n-butyl amine in presence or absence of a solvent and base to provide N-butyl-2-((4R,6S)-6-(hydroxymethyl)-2,2-dimethyl-1,3-dioxan-4-yl)acetamide compound of formula-9,

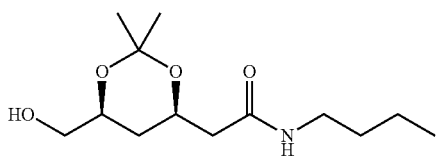

Formula-9 d) oxidizing the compound of formula-9 with a suitable oxidizing agent like sodium hypochlorite in the presence of a catalysts like TEMPO (2,2,6,6-tetramethyl-1-piperidinyloxy, free radical)/KBr or oxalyl chloride/dimethyl sulfoxide in a suitable solvent to provide the N-butyl-2-((4R,6S)-6-formyl-2,2-dimethyl-1,3-dioxan-4-yl)acetamide compound of formula-3a.

In a preferred embodiment of the present invention, the process for the preparation of compound of formula-3a comprises of the following steps,
a) Hydrolyzing the tert-butyl 2-((4R,6S)-6-(hydroxymethyl)-2,2-dimethyl-1,3-dioxan-4-yl)acetate of formula-6 with a suitable base like alkali metal hydroxides, preferably sodium hydroxide in tetrahydrofuran provides the 2-((4R,6S)-6-(hydroxy methyl)-2,2-dimethyl-1,3-dioxan-4-yl) acetic acid compound of formula-7,
b) treating the compound of formula-7 with dimethylsulfate in presence of a suitable base like alkali metal bicarbonate, preferably sodium bicarbonate in a suitable solvent, like alcoholic solvent, preferably methanol to provide the methyl 2-((4R,6S)-6-(hydroxy methyl)-2,2-dimethyl-1,3-dioxan-4-yl)acetate compound of formula-8,
c) reacting the compound of formula-8 with n-butyl amine to provide N-butyl-2-((4R,6S)-6-(hydroxymethyl)-2,2-dimethyl-1,3-dioxan-4-yl)acetamide compound of formula-9,
d) oxidizing the compound of formula-9 with a suitable oxidizing agent preferably sodium hypochlorite in the presence of a catalysts like TEMPO/KBr in a suitable solvent like chloro solvent, preferably methylene chloride provides the N-butyl-2-((4R,6S)-6-formyl-2,2-dimethyl-1,3-dioxan-4-yl)acetamide compound of formula-3a.

The seventh aspect of the present invention provides another process for the preparation of compound of formula-3a, which comprise of the following steps
a) Reacting the ethyl 2-((4R,6S)-6-(acetoxymethyl)-2,2-dimethyl-1,3-dioxan-4-yl)acetate compound of formula-10

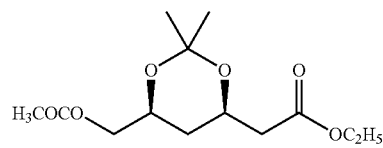

Formula-10 with a suitable base in methanol to provide the methyl 2-((4R,6S)-6-(hydroxy methyl)-2,2-dimethyl-1,3-dioxan-4-yl)acetate compound of formula-8,

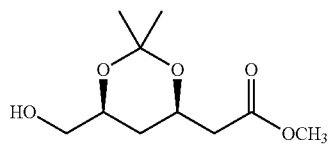

Formula-8 b) reacting the compound of formula-8 with n-butyl amine in the presence or absence of a solvent and base to provide the N-butyl-2-((4R,6S)-6-(hydroxy methyl)-2,2-dimethyl-1,3-dioxan-4-yl)acetamide compound of formula-9,

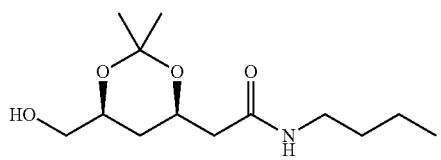

Formula-9 c) oxidizing the compound of formula-9 with a suitable oxidizing agent in the presence or absence of a catalyst in a suitable solvent to provide the N-butyl-2-((4R,6S)-6-formyl-2,2-dimethyl-1,3-dioxan-4-yl)acetamide compound of formula-3a.

In a preferred embodiment of the present invention, the process for the preparation of compound of formula-3a comprises of the following steps,
a) Reacting the ethyl 2-((4R,6S)-6-(acetoxymethyl)-2,2-dimethyl-1,3-dioxan-4-yl)acetate compound of formula-10 with a suitable base like alkali metal carbonate, preferably potassium carbonate in methanol to provide the methyl 2-((4R,6S)-6-(hydroxy methyl)-2,2-dimethyl-1,3-dioxan-4-yl)acetate compound of formula-8,
b) reacting the compound of formula-8 with n-butyl amine in the absence of a solvent and base to provide the N-butyl-2-((4R,6S)-6-(hydroxymethyl)-2,2-dimethyl-1,3-dioxan-4-yl)acetamide compound of formula-9,
c) oxidizing the compound of formula-9 with sodium hypochlorite in the presence of a catalysts like TEMPO/KBr in methylene chloride to provide the N-butyl-2-((4R,6S)-6-formyl-2,2-dimethyl-1,3-dioxan-4-yl)acetamide compound of formula-3a.

Further the present invention provides a process for the preparation of ethyl 2-((4R,6S)-6-(acetoxymethyl)-2,2-dimethyl-1,3-dioxan-4-yl)acetate compound of formula-10,

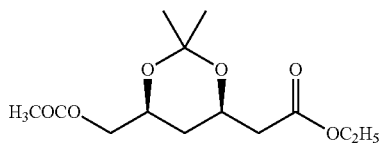
Formula-10 which comprise of the following steps;
a) Reacting the (S)-4-chloro-3-(trimethylsilyloxy)butanenitrile compound of formula-11

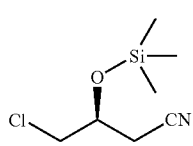
Formula-11 with ethyl bromo acetate compound of formula-12

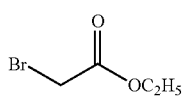
Formula-12 in presence of zinc dust and a suitable acid selected from methane sulfonic acid, para toluene sulfonic acid and the like, preferably methane sulfonic acid in a suitable solvent like tetrahydrofuran to provide the (S)-ethyl 6-chloro-5-hydroxy-3-oxohexanoate compound of formula-13,

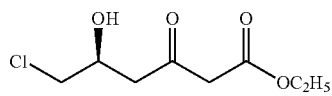
Formula-13 b) reducing the compound of formula-13 by treating it with diethyl methoxy borane in the presence of a suitable reducing agent like sodium borohydride in a suitable solvent selected from alcoholic solvents, polar aprotic solvents, ether solvents or mixtures thereof, preferably mixture of solvent such as methanol and tetrahydrofuran, to provide the (3R,5S)-ethyl 6-chloro-3,5-dihydroxy hexanoate compound of formula-14,

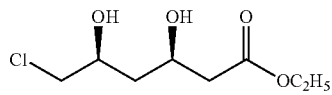
Formula-14 c) treating the (3R,5S)-ethyl 6-chloro-3,5-dihydroxy hexanoate compound of formula-14 with 2,2-dimethoxy propane in the presence of a suitable acid selected from methane sulfonic acid, para toluene sulfonic acid and the like, preferably methane sulfonic acid in a suitable ketone solvent like acetone to provide the ethyl 2-((4R,6S)-6-(chloromethyl)-2,2-dimethyl-1,3-dioxan-4-yl)acetate compound of formula-15,

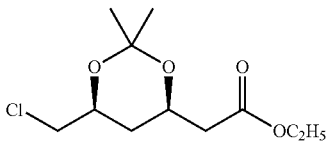
Formula-15 d) reacting the compound of formula-15 with sodium acetate in the presence of a phase transfer catalyst like tetrabutyl ammonium bromide, in presence or absence of a solvent to provide the ethyl 2-((4R,6S)-6-(acetoxymethyl)-2,2-dimethyl-1,3-dioxan-4-yl)acetate compound of formula-10.

The N-butyl-2-((4R,6S)-6-formyl-2,2-dimethyl-1,3-dioxan-4-yl)acetamide compound of formula-3a prepared as per the process described in the above aspects of the present invention can be converted into statin compounds by the methods known, in the art.

Further the present invention also provides a process for the preparation of alkyl 2-((4R,6S)-6-formyl-2,2-dimethyl-1,3-dioxan-4-yl)acetate compound of general formula-16, which comprises of oxidizing the alkyl 2-((4R,6S)-6-(hydroxymethyl)-2,2-dimethyl-1,3-dioxan-4-yl)acetate compounds of general formula-17

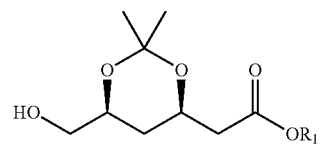
Formula-17 wherein $R_1$ is alkyl as defined above;
with a suitable oxidizing agent preferably with sodium hypochlorite in presence of a catalyst like AZADO(Azaadamantane N-oxyl, free radical)/KBr or 1-Me-AZADO/KBr in a suitable solvent preferably chloro solvents like methylene chloride provides alkyl 2-((4R,6S)-6-formyl-2,2-dimethyl-1,3-dioxan-4-yl)acetate compounds of general formula-16

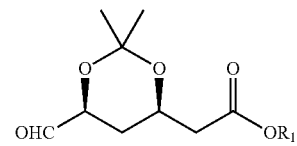
Formula-16 wherein $R_1$ is alkyl as defined above.

As used herein the term "highly pure" refers to the compound with purity greater than 99.00% by HPLC, preferably greater than 99.50% by HPLC and more preferably greater than 99.90% by HPLC.

Related substances and E and Z isomer content of compound of formula-1 and 1a was analyzed by High Performance Liquid Chromatography using the following conditions:
Apparatus: A liquid chromatography is equipped with variable wavelength integrator and detector; Column: Lichrosphere; 250×4.0 mm, 5 μm or equivalent; Flow rate: 1.0 ml/min; Wavelength: 242 nm; Temperature: ambient; Load: 20 μl and using mixture of acetonitrile and water in ratio of 80:20 as a diluent. Mixture of aqueous dihydrogen ortho phosphate buffer and acetonitrile as a mobile phase.

PXRD analysis of compound of formula-1a and formula-5 were carried out using SIEMENS/D-5000 X-Ray diffractometer using Cu, Kα radiation of wavelength 1.54 A° and continuous scan speed of 0.045°/min.

The present invention further schematically represented by the following schemes:
Scheme-1:
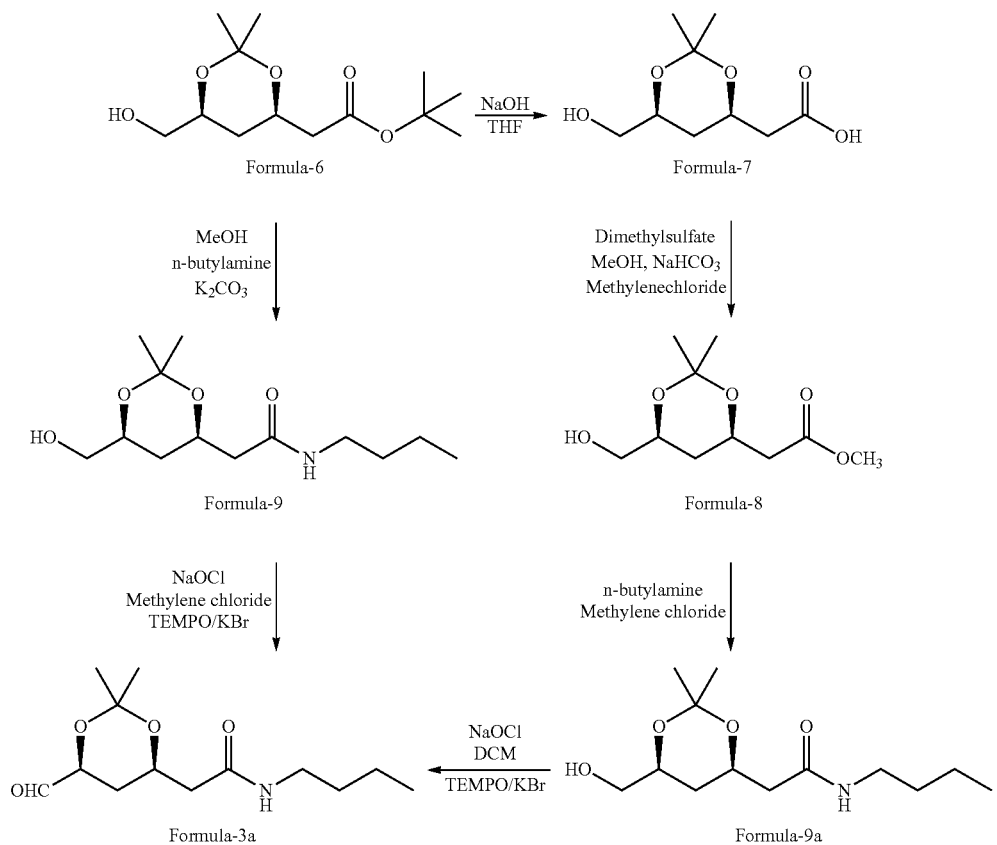
Scheme-2:
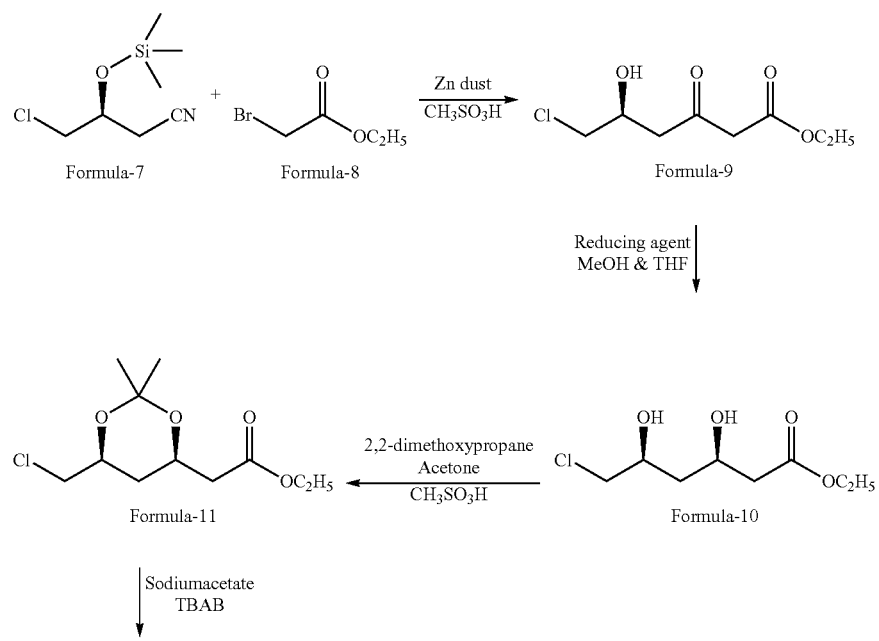

-continued

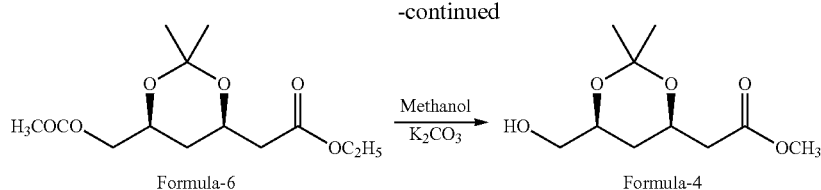

Scheme-3:

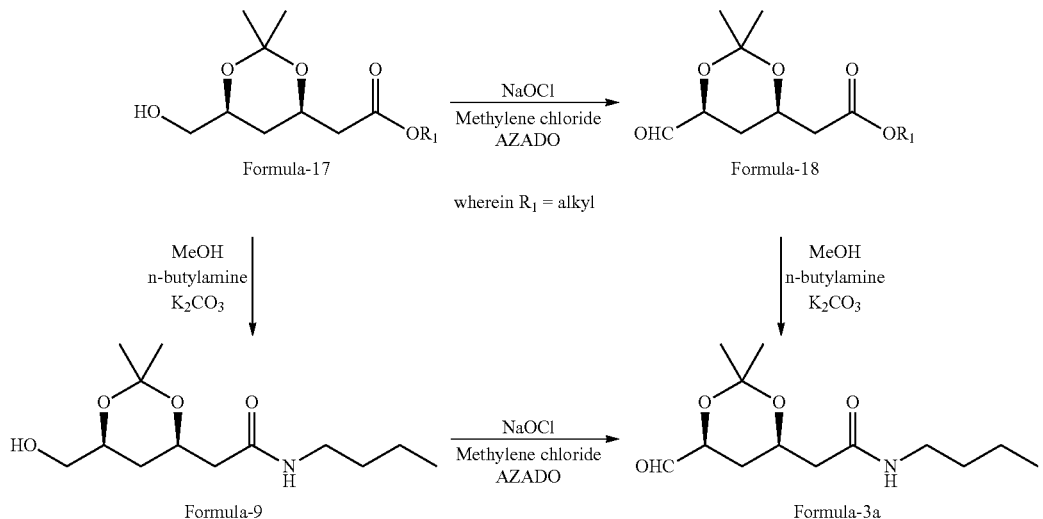

The process described in the present invention was demonstrated in examples illustrated below. These examples are provided as illustration only and therefore should not be construed as limitation of the scope of the invention.

EXAMPLES

Example-1

Preparation of N-butyl-2-((4R,6S)-6-((E)-(4-(4-fluorophenyl)-6-isopropyl-2-(N-methylmethylsulfonamido)pyrimidin-5-yl)vinyl)-2,2-dimethyl-1,3-dioxan-4-yl)acetamide of formula-1a Sodium tertiarybutoxide (3 grams) was added to a mixture of N-(4-(4-fluorophenyl)-6-isopropyl-5-(1-methyl-1H-benzo[d]imidazol-2-ylsulfonyl)pyrimidin-2-yl)-N-methyl-methane sulfonamide (15.5 grams) in tetrahydrofuran (40 ml) at −20 to −15° C. and this mixture was added to a solution of N-butyl-2-(4R,6R)-6-formyl-2,2-dimethyl-1,3-dioxan-4-yl) acetamide in tetrahydrofuran (10 gm) at −20 to −15° C. and stirred. After completion of the reaction, quenched it with sodium bicarbonate solution and stirred for 10 minutes at 5-10° C. The reaction mixture temperature was raised to 25-35° C. and stirred for 4 hours. The solid obtained was filtered, washed with water and then dried to get the title compound.

Yield: 15 grams

Example-2

Preparation of N-butyl-2-((4R,6S)-6-((E)-(4-(4-fluorophenyl)-6-isopropyl-2-(N-methylmethylsulfonamido)pyrimidin-5-yl)vinyl)-2,2-dimethyl-1,3-dioxan-4-yl)acetamide of formula-1a Sodium tertiarybutoxide (4.28 grams) was added to a mixture of N-(4-(4-fluorophenyl)-6-isopropyl-5-(1-methyl-1H-benzo[d]imidazol-2-ylsulfonyl)pyrimidin-2-yl)-N-methyl-methane sulfonamide (15.5 grams) in tetrahydrofuran (40 ml) at −20 to −15° C. and this mixture was added to a solution of N-butyl-2-(4R,6R)-6-formyl-2,2-dimethyl-1,3-dioxan-4-yl) acetamide in tetrahydrofuran (10 gm) at −20 to, −15° C. and stirred. After completion of the reaction, quenched it with sodium bicarbonate solution and stirred for 10 minutes at 5-10° C. The reaction mixture temperature was raised to RT and stirred for 30 minutes. Sodium chloride solution (50 ml) was added to it and extracted the reaction mixture into toluene (80 ml) and stirred for 45 minutes at 0-5° C. The reaction mixture was filtered and washed with toluene. The filtrate was slurried with silica gel and filtered. Distilled off the filtrate completely followed by co-distillation with cyclohexane. Diisopropylether (20 ml) was added to the obtained residue and stirred for 30 minutes at 25-30° C. The solid was filtered, washed with diisopropylether and dried to get the title compound.

Yield: 10 grams

Purity by HPLC: 99.24%; 0.2% (Z isomer)

Example-3

Preparation of N-butyl-2-((4R,6S)-6-((E)-(4-(4-fluorophenyl)-6-isopropyl-2-(N-methylmethylsulfonamido)pyrimidin-5-yl)vinyl)-2,2-dimethyl-1,3-dioxan-4-yl)acetamide of formula-1a Sodium tertiarybutoxide (4.28 grams) was added to a mixture of N-(4-(4-fluorophenyl)-6-isopropyl-5-(1-methyl-1H-benzo[d]imidazol-2-ylsulfonyl)pyrimidin-2-yl)-N-methylmethane sulfonamide (15.5 grams) in tetrahydrofuran (40 ml) at −20 to −15° C. and this mixture was added to a solution of N-butyl-2-(4R,6R)-6-formyl-2,2-dimethyl-1,3-dioxan-4-yl)acetamide in tetrahydrofuran (10 gm) at −20 to −15° C. and stirred. After completion of the reaction, quenched it with chilled water and stirred for 10 minutes at 5-10° C. The reaction mixture temperature was raised to 25-35° C. and stirred for 30 minutes. Sodium chloride solution (50 ml) was added to it and extracted the reaction mixture into toluene (80 ml) and stirred for 45 minutes at 0-5° C. The reaction mixture was filtered and washed with toluene. The filtrate was slurried with silicagel and filtered. Distilled off the filtrate completely followed by codistillation with cyclohexane. Diisopropylether (20 ml) was added to the obtained residue and stirred for 30 minutes at 25-30° C. The solid was filtered, washed with diisopropylether and dried to get the title compound.

Yield: 10 grams

Example-4

Preparation of N-butyl-2-((4R,6S)-6-((E)-(4-(4-fluorophenyl)-6-isopropyl-2-(N-methylmethylsulfonamido)pyrimidin-5-yl)vinyl)-2,2-dimethyl-1,3-dioxan-4-yl)acetamide of formula-1a The title compound is prepared in a similar manner to example-2 except that the final compound is isolated from methanol instead of diisopropylether.

Yield: 9.5 grams

Example-5

Preparation of (3R,5S,E)-N-butyl-7-(4-(4-fluorophenyl)-6-isopropyl-2-(N-methylmethylsulfonamido)pyrimidin-5-yl)-3,5-dihydroxyhept-6-enamide compound of formula-5

Oxalic acid (42.0 grams in 420 ml of water) was added to N-butyl-2-((4R,6S)-6-((E)-(4-(4-fluorophenyl)-6-isopropyl-2-(N-methylmethylsulfonamido) pyrimidin-5-yl)vinyl)-2,2-dimethyl-1,3-dioxan-4-yl)acetamide (175 grams) in methanol (890 ml) at 45-50° C. and stirred at 45-50° C. After completion of the reaction, the reaction mixture was cooled to 5-10° C. and quenched with aqueous ammonia solution. The reaction mixture temperature was raised to 25-30° C. and water was added to it and stirred for 3 hour. The solid obtained was filtered, washed with water and dried to get the title compound.

Yield: 155 grams

Example-6

Purification of (3R,5S,E)-N-butyl-7-(4-(4-fluorophenyl)-6-isopropyl-2-(N-methylmethylsulfonamido)pyrimidin-5-yl)-3,5-dihydroxyhept-6-enamide compound of formula-5

Compound of formula-5 (140 grams) obtained in example-5 was dissolved toluene (980 ml) at 70-75° C. The reaction mixture was slowly cooled to 0-5° C. and stirred for 3 hours. The solid obtained was filtered and washed with toluene. The obtained wet solid was dissolved in a mixture of toluene (880 ml) and acetonitrile (22 ml) at 70-75° C. The reaction mixture was slowly cooled to 0-5° C. and stirred for 3 hours. The obtained solid was filtered, washed with toluene and then dried to get the title compound. The PXRD of obtained solid was shown in FIG. 4.

Yield: 126 grams

Example-7

Preparation of Rosuvastatin Calcium

A mixture of (3R,5S,E)-N-butyl-7-(4-(4-fluorophenyl)-6-isopropyl-2-(N-methyl methylsulfonamido)pyrimidin-5-yl)-3,5-dihydroxyhept-6-enamide of formula-5 (25 grams), isopropyl alcohol (125 ml), aqueous sodium hydroxide (7.5 grams in 75 ml of water) was heated to reflux temperature and stirred at reflux upto completion of the reaction. After completion, the reaction mixture was cooled to 25-30° C. and both organic and aqueous layer was separated. Organic layer was subjected to carbon treatment then filtered through hyflow and washed with isopropylalcohol. The organic layer was distilled off completely under reduced pressure and the obtained residue was cooled to 25-30° C. and water (125 ml) was added to it. The reaction mixture was washed with tertiary butyl acetate. The pH of the reaction mixture was adjusted to 9.2 to with aqueous hydrochloric acid and expel the reaction mixture. The reaction mixture was filtered through filter paper and calcium acetate solution (4.62 grams in 100 ml of water) at 35-40° C. and stirred for 30 minutes. The reaction mixture was cooled to 30-35° C. and stirred for 45 minutes. The solid was filtered, washed with water and then dried at 35-40° C. to get the title compound.

Yield: 20 grams

Example-8

Preparation of Rosuvastatin Calcium

A mixture of (3R,5S,E)-N-butyl-7-(4-(4-fluorophenyl)-6-isopropyl-2-(N-methyl methylsulfonamido)pyrimidin-5-yl)-3,5-dihydroxyhept-6-enamide of formula-5 (25 grams), isopropyl alcohol (125 ml), aqueous sodium hydroxide (7.5 grams in 75 ml of water) was heated to reflux temperature and stirred at reflux upto completion of the reaction. After completion, the reaction mixture was cooled to 25-30° C. and both organic and aqueous layer was separated. Organic layer was subjected to carbon treatment, then filtered through hyflow and washed with isopropylalcohol. The organic layer was distilled off completely under reduced pressure and the obtained residue was cooled to 25-30° C. and water (125 ml) was added to it. The reaction mixture was washed with tertiary butyl acetate. The pH of the reaction mixture was adjusted to 9.1 to with aqueous hydrochloric acid and expel the reaction mixture. The reaction mixture was filtered through filter paper and calcium acetate solution (4.1 grams in 100 ml of water) at 25-29° C. and stirred for 60 minutes. The solid was filtered, washed with water and then dried at 35-40° C. to get the title compound.

Yield: 19.5 grams

Example-9

Preparation of Crystalline Form I of Formula-1a

Sodium tertiarybutoxide (3 grams) was added to a mixture of N-(4-(4-fluorophenyl)-6-isopropyl-5-(1-methyl-1H- benzo[d]imidazol-2-ylsulfonyl)pyrimidin-2-yl)-N-methyl-methane sulfonamide (15.5 grams) in tetrahydrofuran (40 ml) at −20 to −15° C. and this mixture was added to a solution of N-butyl-2-(4R,6R)-6-formyl-2,2-dimethyl-1,3-dioxan-4-yl) acetamide (10 gm) in tetrahydrofuran at −20 to −15° C. and stirred. After the completion of reaction, quenched it will sodium bicarbonate solution and stirred for 10 minutes at 5-10° C. The reaction mixture temperature was raised to RT and stirred for 4 hours. The solid obtained was filtered and washed with water. The wet solid was dissolved in toluene (30 ml) and distilled off under reduced pressure. Cyclohexane was added and co-distilled the solvent completely under reduced pressure. Diisopropyl ether (50 ml) was added to the obtained residue and stirred for an hour 25-35° C. The solid obtained was filtered, washed with diisopropylether and then dried to get the crystalline compound of formula-1a.

Yield: 12.5 grams

Example-10

Preparation of Crystalline Form II of Formula-1a

The compound of formula-1a (10 gm) obtained as per example-1 was dissolved in toluene (50 ml). The solvent from the reaction mixture was distilled off under reduced pressure followed by co-distillation with cyclohexane. Cyclohexane (75 ml) was added to the obtained residue and stirred for an hour at 25-30° C. The solid obtained was filtered, washed with cyclohexane and dried to get the crystalline form II of formula-1a.

Yield: 8.5 grams

Example-11

Preparation of Crystalline Form III of Formula-1a

The crystalline form I of formula-1a (10 gm) was dissolved in methanol (50 ml) and stirred for 10 minutes. Water (50 ml) was added to reaction mixture. The obtained solid was filtered at 25-30° C., washed with water and then dried to get the crystalline form III of formula-1a.

Yield: 8 grams

Example-12

Preparation of N-butyl-2-((4R,6S)-6-((E)-(4-(4-fluorophenyl)-6-isopropyl-2-(N-methylmethylsulfonamido)pyrimidin-5-yl)vinyl)-2,2-dimethyl-1,3-dioxan-4-yl)acetamide of formula-1a Sodium tertiarybutoxide (4.28 grams) was added to a mixture of N-(4-(4-fluorophenyl)-6-isopropyl-5-(1-methyl-1H-benzo[d]imidazol-2-ylsulfonyl)pyrimidin-2-yl)-N-methyl-methane sulfonamide (15.5 grams) in tetrahydrofuran (40 ml) at −20 to −15° C. and this mixture was added to a solution of N-butyl-2-(4R,6R)-6-formyl-2,2-dimethyl-1,3-dioxan-4-yl) acetamide in tetrahydrofuran (10 gm) at −20 to −15° C. and stirred. After completion of the reaction, the reaction mixture was added to chilled water and stirred for 10 minutes at 5-10° C. Toluene (50 ml) was added to the reaction mixture at same temperature and organic layer was separated. The organic layer was washed with sodium chloride solution and then distilled off the solvent from the organic layer under reduced pressure. Toluene (50 ml) was added to the residue, stirred and then filtered. The filtrate was slurried with silicagel and filtered. Distilled off the filtrate completely followed by co-distillation with cyclohexane. Diisopropylether (50 ml) was added to the obtained residue and stirred for 2 hours at 25-30° C. The solid was filtered, washed with diisopropylether and dried to get the title compound.

Yield: 9 grams
Purity by HPLC: 99.27%; 0.15% (Z isomer).

Example-13

Preparation of (S)-ethyl 6-chloro-5-hydroxy-3-oxohexanoate

Mixture of zinc dust (69 grams) and methane sulfonic acid (6 ml) in tetrahydrofuran (500 ml) was heated to reflux temperature and stirred for an hour. (S)-4-chloro-3-(trimethylsilyloxy)butanenitrile (100 grams) followed by ethyl bromo acetate (147.2 grams) was added to the reaction mixture at 65-70° C. and stirred. After completion of the reaction, the reaction mixture was cooled to 25-30° C. and then added to the aqueous hydrochloric acid solution at 0° C. and stirred. The reaction mixture extracted into ethyl acetate and then washed it with sodium bicarbonate solution followed by sodium chloride solution. Ethyl acetate was distilled off from the reaction mixture under reduced pressure to get the title compound.

Yield: 116 grams

Example-14

Preparation of (3R,5S)-ethyl 6-chloro-3,5-dihydroxyhexanoate

Diethyl methoxy borane (88 ml) followed by sodium borohydride (16 grams) was added to a pre-cooled mixture of (S)-ethyl 6-chloro-5-hydroxy-3-oxohexanoate (110 grams) in tetrahydrofuran (550 ml) and methanol (220 ml) at −75° C. under nitrogen atmosphere and stirred for 2 hrs. The reaction mixture was quenched with 50% hydrogen peroxide at 0° C. The reaction mixture was extracted into methylene chloride and washed it with 10% sodium bicarbonate followed by saturated sodium chloride solution. The methylene chloride layer was dried with sodium sulfate and distilled off under reduced pressure to get the title compound.

Yield: 82 grams

Example-15

Preparation of ethyl 2-((4R,6S)-6-(chloro methyl)-2,2-dimethyl-1,3-dioxan-4-yl)acetate 2,2-dimethoxy propane (180 grams) followed by methane sulfonic acid (1.1 ml) was added to a mixture of (3R,5S)-ethyl 6-chloro-3,5-dihydroxy hexanoate (80 grams) and acetone (400 ml) at 25-30° C. and stirred. After completion of the reaction, quenched it with sodium bicarbonate solution and stirred. The reaction mixture was extracted in to petroleum ether and the washed it with saturated sodium chloride solution. The petroleum ether from the reaction mixture was distilled off under reduced pressure to get the title compound.

Yield: 60 grams

Example-16

Preparation of ethyl 2-((4R,6S)-6-(acetoxymethyl)-2,2-dimethyl-1,3-dioxan-4-yl)acetate Mixture of ethyl 2-((4R,6S)-6-(chloromethyl)-2,2-dimethyl-1,3-dioxan-4-yl)acetate (60 grams), tetra butyl ammonium bromide (79 grams) and anhydrous sodium acetate (61.2 grams) was heated to reflux temperature and stirred. After the completion of the reaction, the reaction mixture was cooled to 25-30° C. and petroleum ether (50 ml) was added to it then stirred for 60 minutes at 25-30° C. The reaction mixture was filtered and washed with petroleum ether. The solvent from the filtrate was distilled off under reduced pressure to get the title compound.

Yield: 31 grams

Example-17

Preparation of methyl 2-((4R,6S)-6-(hydroxymethyl)-2,2-dimethyl-1,3-dioxan-4-yl)acetate Mixture of ethyl 2-((4R,6S)-6-(acetoxymethyl)-2,2-dimethyl-1,3-dioxan-4-yl)acetate (80 grams), potassium carbonate (21 grams) in methanol (400 ml) was stirred for 2 hours at 0-10° C. The reaction mixture was quenched with water and then the reaction mixture extracted into methylene chloride and washed it with water. The methylene chloride from the reaction mixture was distilled off under reduced pressure to get the title compound.

Yield: 64 grams

Example-18

Preparation of N-butyl-2-((4R,6S)-6-(hydroxymethyl)-2,2-dimethyl-1,3-dioxan-4-yl)acetamide Mixture of n-butyl amine (100 grams), methyl 2-((4R,6S)-6-(hydroxymethyl)-2,2-dimethyl-1,3-dioxan-4-yl)acetate (20 grams) was heated to reflux and stirred. After completion of the reaction, distilled off n-butylamine under reduced pressure at below 60° C. The obtained residue was further purified using mixture of cyclohexane and ethyl acetate.

Yield: 17 grains

Example-19

Preparation of N-butyl-2-((4R,6S)-6-formyl-2,2-dimethyl-1,3-dioxan-4-yl)acetamide A solution of N-butyl-2-((4R,6S)-6-(hydroxymethyl)-2,2-dimethyl-1,3-dioxan-4-yl) acetamide (6 grams) in methylene chloride (24 ml) was added to a pre-cooled mixture of TEMPO (0.01 gram), methylene chloride (36 ml) and potassium bromide (0.26 grams) at −5 to −15° C. Sodium hypo chlorite (15.6 ml) was added to the reaction mixture at −15 to −5° C. and stirred. After completion of the reaction, quenched it with 10% sodium thio sulfate solution at room temperature and water was added to it. Both organic and aqueous layers were separated and organic layer was washed with water followed by saturated sodium chloride solution. The solvent from organic layer was distilled off under reduced pressure to get the title compound.

Yield: 2.5 grams

Example-20

Preparation of N-butyl-2-((4R,6S)-6-formyl-2,2-dimethyl-1,3-dioxan-4-yl)acetamide N-butyl-2-((4R,6S)-6-(hydroxymethyl)-2,2-dimethyl-1,3-dioxan-4-yl)acetamide (2 grams) in methylene chloride (10 ml) was added a mixture of oxalyl chloride (1.46 grams), dimethyl sulfoxide (1.36 ml) and methylene chloride (12 ml) at −65 to −60° C. under nitrogen atmosphere and stirred for 45 minutes. Triethylamine (5 ml) was added to the reaction mixture at −65 to −60° C., stirred for 60 minutes and then added to ice-water. The reaction mixture was acidified with acetic acid solution and stirred. Both organic and aqueous layers were separated and organic layer washed with water followed by sodium chloride solution. The solvent from organic layer was distilled off under reduced pressure to get the title compound.

Yield: 1.8 grams

Example-21

Preparation of 2-((4R,6S)-6-(hydroxymethyl)-2,2-dimethyl-1,3-dioxan-4-yl)acetic acid Mixture of tert-butyl 2-((4R,6S)-6-(hydroxymethyl)-2,2-dimethyl-1,3-dioxan-4-yl)acetate (200 grams), sodium hydroxide (62 grams) in tetrahydrofuran (400 ml) was heated to reflux temperature and stirred up to completion of the reaction. The solvent from the reaction mixture was distilled off completely under reduced pressure at below 70° C. to get the title compound.

Yield: 300 grams

Example-22

Preparation of methyl 2-((4R,6S)-6-(hydroxymethyl)-2,2-dimethyl-1,3-dioxan-4-yl)acetate Dimethyl sulfate (195 grams) was added to a mixture of 2-((4R,6S)-6-(hydroxymethyl)-2,2-dimethyl-1,3-dioxan-4-yl)acetic acid (200 grams), methanol (800 ml) and sodium bicarbonate (50 grams) at 0° C. and stirred for 12 hours at 25-30° C. After completion of the reaction, reaction mixture was quenched with water and extracted into methylene chloride. The methylene chloride was distilled off from the reaction mixture under reduced pressure to get the title compound.

Yield: 108 grams.

Example-23

Preparation of N-butyl-2-((4R,6S)-6-(hydroxymethyl)-2,2-dimethyl-1,3-dioxan-4-yl)acetamide A mixture of methyl 2-((4R,6S)-6-(hydroxymethyl)-2,2-dimethyl-1,3-dioxan-4-yl)acetate (110 grams) and n-butylamine (370 grams) was heated to reflux and stirred. After completion of the reaction, the reaction mixture was distilled under reduced pressure. Water (500 ml) was added to the obtained residue followed by sodium bicarbonate and washed it with petroleum ether. The reaction mixture was extracted into methylene chloride. The solvent from the reaction mixture was distilled off under reduced pressure to get the title compound.

Yield: 99 grams

Example-24

Preparation of N-butyl-2-((4R,6S)-6-(hydroxymethyl)-2,2-dimethyl-1,3-dioxan-4-yl)acetamide A mixture of tert-butyl 2-((4R,6S)-6-(hydroxymethyl)-2,2-dimethyl-1,3-dioxan-4-yl)acetate (10 grams), methanol (80 ml), n-butyl amine (20 ml) and potassium carbonate (10.6 grams) was heated to 40-45° C. and stirred up to completion of the reaction. The reaction mixture was distilled under reduced pressure and methylene chloride (100 ml) was added to the obtained residue at 25-30° C. and stirred for 15 minutes. The unwanted solid was filtered off and the filtrate was distilled off under reduced pressure to get the title compound.

Yield: 7 grams

Example-25

Preparation of N-butyl-2-((4R,6S)-6-(hydroxymethyl)-2,2-dimethyl-1,3-dioxan-4-yl)acetamide Mixture of tert-butyl 2-((4R,6S)-6-(hydroxymethyl)-2,2-dimethyl-1,3-dioxan-4-yl)acetate (50 grams), methanol (300 ml) and n-butyl amine (200 ml) was heated to 60-70° C. under nitrogen pressure and stirred. After the completion of the reaction, distilled off the reaction mixture completely followed by co-distillation with methylene chloride at below 55° C. Methylene chloride (500 ml) was added to the obtained residue at 25-30° C. and stirred for 15 minutes. The unwanted solid was filtered off and the filtrate was distilled off under reduced pressure to get the title compound.

Yield: 36 grams

Example-26

Preparation of N-butyl-2-((4R,6S)-6-(hydroxymethyl)-2,2-dimethyl-1,3-dioxan-4-yl)acetamide A mixture of tert-butyl 2-((4R,6S)-6-(hydroxymethyl)-2,2-dimethyl-1,3-dioxan-4-yl)acetate (10 grams), methanol (80 ml), n-butyl amine (20 ml) and potassium carbonate (10.6 grams) was heated to 40-45° C. and stirred up to completion of the reaction. The reaction mixture was distilled under reduced pressure and methylene chloride (100 ml) was added to the obtained residue at 25-30° C. and stirred for 15 minutes. The unwanted solid was filtered off and the filtrate was distilled off under reduced pressure. The obtained residue was dissolved in methylene chloride (32 ml) and a mixture of TEMPO (0.015 grams), potassium bromide (0.36 grams) in methylene chloride (48 ml) was added to it and stirred for 15 minutes. Sodium hypochlorite solution (20.8 ml) was added to the reaction mixture at −15 to 15° C. and stirred for an hour. After completion of the reaction, the reaction mixture was quenched with sodium thio sulfate solution at below 10° C. Both organic and aqueous layers were separated and aqueous layer extracted with methylene chloride. The solvent from organic layer was distilled off under reduced pressure to get the title compound.

Yield: 5 grams.

Example-27

Preparation of N-butyl-2-((4R,6S)-6-(hydroxymethyl)-2,2-dimethyl-1,3-dioxan-4-yl)acetamide A mixture of tert-butyl 2-((4R,6S)-6-(hydroxymethyl)-2,2-dimethyl-1,3-dioxan-4-yl)acetate (10 grams), methanol (80 ml), n-butyl amine (20 ml) and potassium carbonate (10.6 grams) was heated to 40-45° C. and stirred up to completion of the reaction. The reaction mixture was distilled under reduced pressure and methylene chloride (100 ml) was added to the obtained residue at 25-30° C. and stirred for 15 minutes. The unwanted solid was filtered off and the filtrate was distilled off under reduced pressure. The obtained residue was dissolved in methylene chloride (32 ml) and a mixture of AZADO (0.002 grams), potassium bromide (0.44 grams) in methylene chloride (48 ml) was added to it and stirred for 15 minutes. Sodium hypochlorite solution (20.8 ml) was added to the reaction mixture at −15 to 15° C. and stirred for an hour. After completion of the reaction, the reaction mixture was quenched with sodium thio sulfate solution at below 10° C. Both organic and aqueous layers were separated and aqueous layer extracted with methylene chloride. The solvent from organic layer was distilled off under reduced pressure to get the title compound.

Yield: 4.8 grams

Example-28

Preparation of tert-butyl 2-((4R,6S)-6-formyl-2,2-dimethyl-1,3-dioxan-4-yl)acetate To the −15° C. to −5° C. pre-cooled reaction mixture of AZADO (0.002 g), potassium bromide (0.22 g) and methylene chloride (30 ml) added 5 g of tert-butyl 2-((4R,6S)-6-(hydroxymethyl)-2,2-dimethyl-1,3-dioxan-4-yl)acetate. Stirred the reaction mixture for 15 minutes at −15° C. to −5° C. 19 ml of sodium hypochlorite solution was added to the reaction mixture at same temperature. Stirred the reaction mixture for 15 minutes. Quenched the reaction mixture with 10% aqueous sodium thiosulfate solution. 20 ml of water was added and separated the both aqueous and organic layers. Washed the organic layer with water followed by brine solution. Distilled off the solvent completely to get the title compound as a solid.

Yield: 4.1 grams

Example-28

Preparation of N-butyl-2-((4R,6S)-6-(hydroxymethyl)-2,2-dimethyl-1,3-dioxan-4-yl)acetamide Mixture of tert-butyl 2-((4R,6S)-6-(hydroxymethyl)-2,2-dimethyl-1,3-dioxan-4-yl)acetate (100 grams), methanol (1 L), n-butyl amine (200 ml) and sodium, tertiary butoxide (74 grams) was heated to 40-45° C. and stirred up to completion of the reaction. Distilled off the reaction mixture completely under reduced pressure and water (300 ml) was added to it at 25-30° C. The reaction mixture was cooled and acidified with aqueous acetic acid. The reaction mixture washed with cyclohexane and product from aqueous layer was extracted into methylene chloride. The organic layer was washed with saturated sodium chloride solution and the solvent from it was distilled off under reduced pressure to get the title compound.

Yield: 59 grams

We claim:

1. A process for the preparation of a compound of Formula-1 having E/Z isomer content in a ratio of at least 97:3, Formula-1

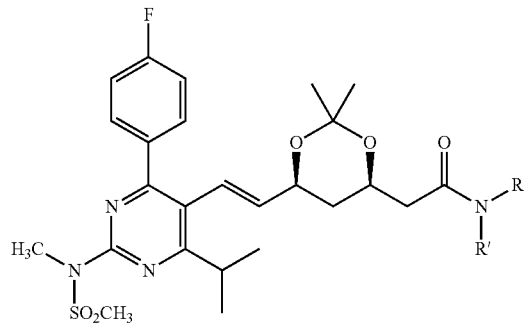

wherein R and R' are independently selected from hydrogen, alkyl, aryl or aralkyl;
the process comprising:
reacting a compound of Formula-2

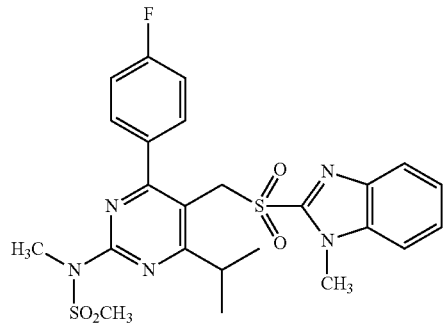

Formula-2 with a compound of Formula-3

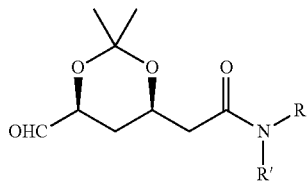

Formula-3 wherein R and R' are independently selected from hydrogen, alkyl, aryl or aralkyl;
in the presence of an alkali metal alkoxide base in a suitable solvent to provide the compound of Formula-1, wherein the alkoxide base is used in the mole ratio of 0.8 to 2.5 moles with respect to the compound of Formula-2.

2. The process according to claim 1, wherein the alkali metal alkoxide base is sodium methoxide, potassium methoxide, sodium tertiary butoxide or potassium tertiary butoxide, and the solvent is a polar aprotic solvent, an alcohol solvent, a hydrocarbon solvent, a polar solvent or an ether solvent.

3. The process according to claim 1, wherein the reaction is carried out at a temperature ranging from −20° C. to 40° C.

4. A process for the preparation of crystalline compound of Formula-1a having E/Z isomer content in a ratio of at least 97:3,

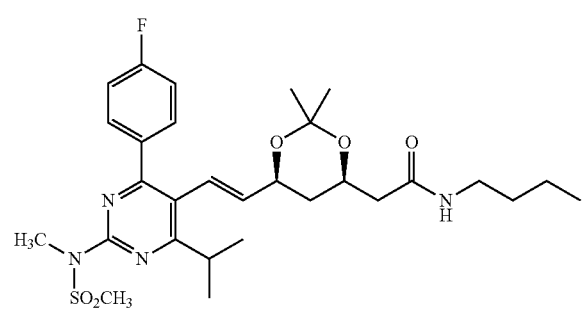

Formula-1a the process comprising:
reacting a compound of Formula-2

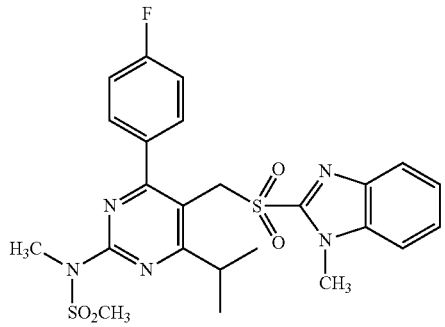

Formula-2 with a compound of Formula-3a

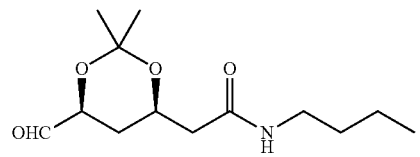

Formula-3a in the presence of sodium or potassium tertiary butoxide in tetrahydrofuran at a temperature of −20° C. to 40° C. to provide the compound of Formula-1a, and purifying the compound of Formula-1a with a suitable solvent to provide crystalline compound of Formula-1a.

5. The process of claim 4, wherein the crystalline compound of Formula-1a is a crystalline Form-I of the compound of Formula-1a and is characterized by its powder X-ray diffractogram having peaks at about 5.56, 7.47. 8.40. 9.78, 14.75, 16.80, 17.46, 18.72, 20.05, 21.13, 21.70, 23.13, 25.57, 31.68 and 45.35±0.2 degrees 2θ; and wherein purifying the compound of Formula-1a comprises:
 a) dissolving the compound of Formula-1a in toluene to form a reaction mixture;
 b) concentrating the reaction mixture of step (a) followed by co-distillation with cyclohexane to form a residue;
 c) adding diisopropylether to the residue;
 d) stirring the reaction mixture of step (c);
 e) filtering the solid produced in step (d) and washing with diisopropylether; and
 f) drying the solid to get the crystalline Form-I of Formula-1a.

6. The process of claim 4, wherein the crystalline compound of Formula-1a is a crystalline Form-II of the compound of Formula-1a and is characterized by its powder X-ray diffractogram having peaks at about 3.74, 7.37, 8.17, 14.69, 15.05, 17.25, 17.75, 18.42, 18.77, 19.20, 20.59, 22.42, 22.69, 23.67 and 28.01±0.2 degrees 2θ; and wherein purifying the compound of Formula-1a comprises:
 a) dissolving the compound of Formula-1a in toluene to form a reaction mixture;
 b) concentrating the reaction mixture of step (a) followed by co-distillation with cyclohexane to form a residue;
 c) adding cyclohexane to the residue;
 d) stirring the reaction mixture of step (c);
 e) filtering the solid produced in step (d) and washing with cyclohexane; and f) drying the solid to get the crystalline Form-II of Formula-1a.

7. The process of claim 4, wherein the crystalline compound of Formula-1a is a crystalline Form-III of the compound of Formula-1a and is characterized by its powder X-ray diffractogram having peaks at about 5.56, 8.43, 9.58, 9.89, 14.65, 15.18, 16.76, 17.43, 18.75, 19.26, 19.90, 20.21, 21.11, 21.63, 22.30, 25.45 and 27.93±0.2 degrees 2θ; and wherein purifying the compound of Formula-1a comprises:
 a) dissolving the compound of Formula-1a in an alcohol solvent;
 b) adding water to the reaction mixture;
 c) filtering the solid produced in step (b) and washing with water; and
 d) drying the solid to get the crystalline Form-III of Formula-1a.

8. The process according to claim 4, further comprising:
a) hydrolyzing a compound of Formula-6

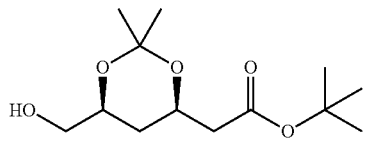

Formula-6 with a suitable base in a suitable solvent, to provide a compound of Formula-7,

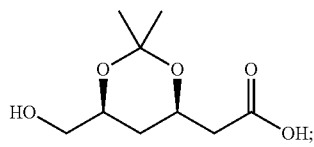

Formula-7 b) treating the compound of Formula-7 with dimethylsulfate in presence of a suitable base in a suitable solvent to provide a compound of Formula-8,

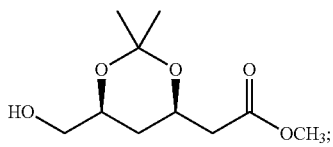

Formula-8 c) reacting the compound of Formula-8 with n-butyl amine in presence or absence of a suitable solvent and suitable base to provide a compound of Formula-9,

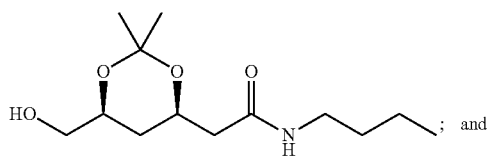

Formula-9 d) oxidizing the compound of Formula-9 with sodium hypochlorite in presence of a catalyst selected from TEMPO (2,2,6,6-tetramethyl-1-piperidinyloxy)/KBr or oxalyl chloride/dimethyl sulfoxide or AZADO(Azaadamantane N-oxyl)/KBr in a suitable solvent to provide the compound of Formula-3a.

9. The process of claim 8, wherein the compound of Formula-3a is prepared by the process comprising:
 a) hydrolyzing the compound of Formula-6 with an alkali metal hydroxide in an ether solvent to provide the compound of Formula-7;
 b) treating the compound of Formula-7 with dimethylsulfate in presence of an alkali metal bicarbonate in methanol to provide the compound of Formula-8;
 c) reacting the compound of Formula-8 with n-butyl amine in presence or absence of a suitable solvent and suitable base to provide the compound of Formula-9; and
 d) oxidizing the compound of Formula-9 with sodium hypochlorite in presence of TEMPO/KBr in a chloro solvent to provide the compound of Formula-3a.

10. The process of claim 8, wherein the compound of Formula-3a is prepared by the process comprising:
 a) hydrolyzing the compound of Formula-6, with a suitable base in a suitable solvent to provide the compound of Formula-7;
 b) treating the compound of Formula-7 with dimethylsulfate in presence of a suitable base in methanol to provide the compound of Formula-8;
 c) reacting the compound of Formula-8 with n-butylamine in presence or absence of a suitable solvent and suitable base to provide the compound of Formula-9; and
 d) oxidizing the compound of Formula-9 with sodium hypochlorite in presence of AZADO/KBr in methylene chloride to provide the compound of Formula-3a.

11. The process of claim 4, further comprising:
reacting a compound of Formula-6

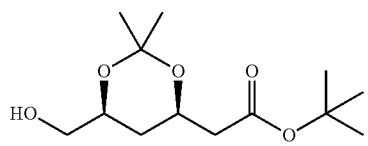

Formula-6 with n-butyl amine in methanol in the presence or absence of a suitable base to provide a compound of Formula-9,

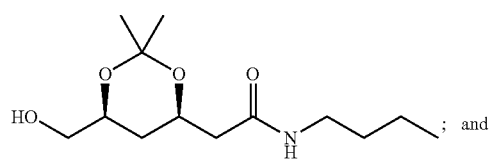

Formula-9 oxidizing the compound of Formula-9 with sodium hypochlorite in presence of a catalyst selected from TEMPO (2,2,6,6-tetramethyl-1-piperidinyloxy)/KBr or oxalyl chloride/dimethyl sulfoxide or AZADO (Azaadamantane N-oxyl)/KBr in a suitable solvent to provide the compound of Formula-3a.

12. The process of claim 8, wherein the compound of Formula-8 is prepared by the process comprising: reacting the compound of Formula-7 with dimethylsulfate in presence of a suitable base in methanol to provide the compound of Formula-8.

13. The process of claim 4, wherein the compound of Formula-3a is prepared by the process comprising:

a) reacting a compound of Formula-10

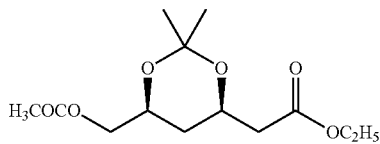

Formula-10 with a suitable base in methanol to provide a compound of Formula-8,

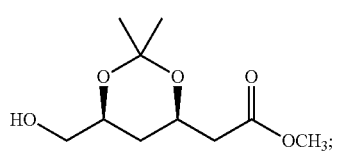

Formula-8 b) reacting the compound of Formula-8 with n-butyl amine in presence or absence of a suitable solvent and suitable base to provide a compound of Formula-9,

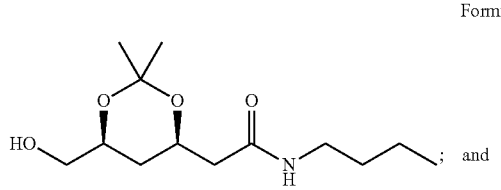

Formula-9

; and c) oxidizing the compound of Formula-9 with sodium hypochlorite in presence of a catalyst selected from TEMPO (2,2,6,6-tetramethyl-1-piperidinyloxy)/KBr or oxalyl chloride/dimethyl sulfoxide or AZADO(Azaadamantane N-oxyl)/KBr in a suitable solvent to provide the compound of Formula-3a.

14. The process according to claim 4, further comprising:

a) reacting a compound of Formula-6

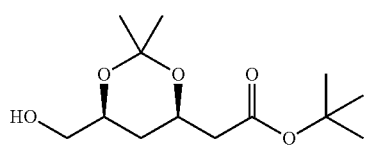

Formula-6 with n-butyl amine in presence of an alkali metal carbonate in methanol to provide a compound of Formula-9,

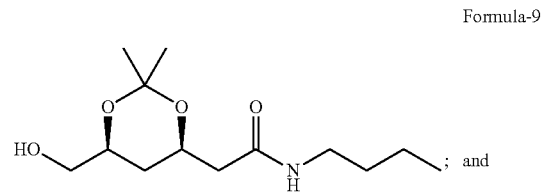 [SMILES: CCCCNC(=O)C[C@H]1C[C@@H](CO)OC(C)(C)O1]

Formula-9

; and b) oxidizing the compound of Formula-9 with sodium hypochlorite in presence of a catalyst selected from TEMPO (2,2,6,6-tetramethyl-1-piperidinyloxy)/KBr or oxalyl chloride/dimethyl sulfoxide or AZADO(Azaadamantane N-oxyl)/KBr in a suitable solvent to provide the compound of Formula-3a.

* * * * *